(12) United States Patent
Kendall et al.

(10) Patent No.: US 6,841,382 B2
(45) Date of Patent: Jan. 11, 2005

(54) HUMAN RECEPTOR TYROSINE KINASE, KDR

(75) Inventors: Richard L. Kendall, Doylestown, PA (US); Kenneth A. Thomas, Chatham Borough, NJ (US); Xianzhi Mao, Rockledge, PA (US); Andrew Tebben, Harleysville, PA (US)

(73) Assignee: Merck & Co., Inc., Rahway, NJ (US)

( * ) Notice: Subject to any disclaimer, the term of this patent is extended or adjusted under 35 U.S.C. 154(b) by 63 days.

(21) Appl. No.: 10/022,939

(22) Filed: Dec. 18, 2001

(65) Prior Publication Data

US 2003/0032160 A1 Feb. 13, 2003

Related U.S. Application Data

(62) Division of application No. 09/483,539, filed on Jan. 14, 2000, now Pat. No. 6,359,115, which is a division of application No. 09/098,707, filed on Jun. 17, 1998, now Pat. No. 6,204,011.
(60) Provisional application No. 60/050,962, filed on Jun. 18, 1997.

(51) Int. Cl.$^7$ .............................. C12N 5/10; C07K 14/71
(52) U.S. Cl. ..................... 435/325; 435/69.1; 435/69.7; 435/183; 435/252.3; 435/254.11; 530/350; 536/23.5; 536/23.4
(58) Field of Search ......................... 530/350; 435/325, 435/252.3, 254.11, 69.4, 69.1, 69.7, 183; 536/23.5, 23.4

(56) References Cited

U.S. PATENT DOCUMENTS

| | | | |
|---|---|---|---|
| 5,240,848 A | | 8/1993 | Keck et al. |
| 5,332,671 A | | 7/1994 | Ferrara et al. |
| 5,766,860 A | * | 6/1998 | Terman et al. |
| 5,861,301 A | * | 1/1999 | Terman et al. |

FOREIGN PATENT DOCUMENTS

| | | |
|---|---|---|
| EP | 0 506 477 A1 | 3/1992 |
| WO | WO 92/14748 | 9/1992 |
| WO | WO 9214748 A1 * | 9/1992 |
| WO | WO 94/11499 | 5/1994 |

OTHER PUBLICATIONS

Ferrara, N. et al; The Vascular Endothelial Growth Factor Family of Polypeptides; Journal of Cellular Biochemistry, vol. 47; 1991; pp. 211–218.

Maglione, D. et al; Two Alternative mRNAs coding for the angiogenic factor, placenta growth factor (PlGF), Are Transcribed from a Single Gene of chromosome 14; Oncogene; vol. 8, 1993, p. 925–931.

Hauser, S. et al.; A Heparin–Binding Form of Placenta; Growth Factor (PlGF–2) is Expressed in Human Umbilical Vein Endothelial Cells and in Placenta; Growth Factors; vol. 9, 1993; pp. 259–268.

Grimmond, S. et al; Cloning and Characterization of a Novel Human Gene Related to Vascular Endothelial Growth Factor; Genome Research; vol. 6, 1996; pp. 124–131.

Olofsson, B. et al; Vascular Endothelial Growth Factor B, A Novel Growth Factor for Endothelial cells; Proc. Natl. Acad Sci. USA, vol. 93, 1996; pp. 2576–2581.

Joukov, V. et al; A Novel Vascular Endothelial Growth Factor, VEGF–C is a Ligand for the FLT (VEGFR–3) and KDR (VEGFR–2) Receptor Tyrosine Kinases; The EMBO Journal; vol. 15; No. 2; 1996; pp. 290–298.

Shibuya, M. et al. Nucleotide Sequence and Expression of a Novel Human Receptor–Type Tyrosine Kinase Gene (FLT) closely Related to the fms Family; Oncogene; vol. 5, 1990, pp. 519–524.

Pajusola, K. et al, FLT4 Receptor Tyrosine Kinase Contains Seven Immunoglobin–like Loops and Is Expressed in Multiple Human Tissues and Cell Lines; Cancer Research; vol. 52, 5738–5743.

Terman, B.I. et al; Identification of a New Endothelial Cell Growth Factor Receptor Tyrosine Kinase; Oncogene; vol. 6, 1991, pp. 1677–1683.

Terman, B.J. et al; Identification of the KDR Tyrosine Kinase as a Receptor for Vascular Endothelial Cell Growth Factor, Biochemical & Biophysical Research Communications; vol. 187, No. 3; 1992; pp. 1579–1586.

Rockwell et al. 'In Vitro Neutralization . . . Monoclonal Antibody', Mol. Cell Differ., vol. 3(1), pp. 91–109 (1995).

* cited by examiner

*Primary Examiner*—Elizabeth Kemmerer
*Assistant Examiner*—Claire M. Kaufman
(74) *Attorney, Agent, or Firm*—Yang Xu; Jack L. Tribble

(57) ABSTRACT

An isolated nucleic acid molecule encoding a novel human receptor type tyrosine kinase gene, KDR, is disclosed. The isolation of this KDR cDNA sequence results in disclosure of purified forms of human KDR protein, recombinant vectors and recombinant hosts which express human KDR.

6 Claims, 6 Drawing Sheets

```
ATGGAGAGCAAGGTGCTGCTGGCCGTCGCCCTGTGGCTCTGCGTGGAGACCC
GGGCCGCCTCTGTGGGTTTGCCTAGTGTTTCTCTTGATCTGCCCAGGCTCAGCA
TACAAAAAGACATACTTACAATTAAGGCTAATACAACTCTTCAAATTACTTGCAG
GGGACAGAGGGACTTGGACTGGCTTTGGCCCAATAATCAGAGTGGCAGTGAG
CAAAGGGTGGAGGTGACTGAGTGCAGCGATGGCCTCTTCTGTAAGACACTCAC
AATTCCAAAAGTGATCGGAAATGACACTGGAGCCTACAAGTGCTTCTACCGGG
AAACTGACTTGGCCTCCGTCATTTATGTCTATGTTCAAGATTACAGATCTCCATT
TATTGCTTCTGTTAGTGACCAACATGGAGTCGTGTACATTACTGAGAACAAAAA
CAAAACTGTGGTGATTCCATGTCTCGGGTCCATTTCAAATCTCAACGTGTCACTT
TGTGCAAGATACCCAGAAAAGAGATTTGTTCCTGATGGTAACAGAATTTCCTGG
GACAGCAAGAAGCGGCTTTACTATTCCCAGCTAGATGATCAGCTATGCTGGCATG
GTCTTCTGTGAAGCAAAAATTAATGATGAAAGTTACCAGTCTATTATGTACATAG
TTGTCGTTGTAGGGTATAGGATTTATGATGTGGTTCTGAGTCCGTCTCATGGAA
TTGAACTATCTGTTGGAGAAAAGCTTGTCTTAAATTGTACAGCAAGAACTGAAC
TAAATGTGGGGATTGACTTCAACTGGGAATACCCTTCTTCGAAGCATCAGCATA
AGAAACTTGTAAACCGAGACCTAAAAACCCAGTCTGGGAGTGAGATGAAGAAA
TTTTTGAGCACCTTAACTATAGATGGTGTAACCCGGAGTGACCAAGGATTGTAC
ACCTGTGCAGCATCCACTGGGCTGATGACCAAGAAGAACAGCACATTTGTCAG
GGTCCATGAAAAACCTTTTGTTGCTTTTGGAAGTGGCATGGAATCTCTGGTGGA
AGCCACGGTGGGGGAGCGTGTCAGAATCCCTGCGAAGTACCTTGGTTACCCAC
CCCCAGAAATAAAATGGTATAAAAATGGAATACCCCTTGAGTCCAATCACACAA
TTAAAGCGGGGCATGTACTGACGATTATGGAAGTGAGTGAAAGAGACACAGGA
AATTACACTGTCATCCTTACCAATCCCATTTCAAAGGAGAAGCAGAGCCATGTG
GTCTCTCTGGTTGTGTATGTCCCACCCCAGATTGGTGAGAAATCTCTAATCTCTC
CTGTGGATTCCTACCAGTACCGGCACCACTCAAACGCTGACATGTACGGTCTATG
CCATTCCTCCCCCGCATCACATCCACTGGTATTGGCAGTTGGAGGAAGAGTGC
GCCAACGAGCCCAGCCAAGCTGTCTCAGTGACAAACCCATACCCTTGTGAAGA
ATGGAGAAGTGTGGAGGACTTCCAGGGAGGAAATAAAATTGAAGTTAATAAAA
ATCAATTTGCTCTAATTGAAGGAAAAAACAAAACTGTAAGTACCCTTGTTATCCA
AGCGGCAAATGTGTCAGCTTTGTACAAATGTGAAGCGGTCAACAAAGTCGGGA
GAGGAGAGAGGGTGATCTCCTTCCACGTGACCAGGGGTCCTGAAATTACTTTG
CAACCTGACATGCAGCCCACTGAGCAGGAGAGCGTGTCTTTGTGGTGCACTGC
AGACAGATCTACGTTTGAGAACCTCACATGGTACAAGCTTGGCCCACAGCCTCT
GCCAATCCATGTGGGAGAGTTGCCCACACCTGTTTGCAAGAACTTGGATACTCT
TTGGAAATTGAATGCCACCATGTTCTCTAATAGCACAAATGACATTTTGATCATG
GAGCTTAAGAATGCATCCTTGCAGGACCAAGGAGACTATGTCTGCCTTGCTCAA
GACAGGAAGACCAAGAAAAGACATTGCGTGGTCAGGCAGCTCACAGTCCTAGA
GCGTGTGGCACCCACGATCACAGGAAACCTGGAGAATCAGACGACAAGTATTG
GGGAAAGCATCGAAGTCTCATGCACGGCATCTGGGAATCCCCCTCCACAGATC
ATGTGGTTTAAAGATAATGAGACCCTTGTAGAAGACTCAGGCATTGTATTGAAG
GATGGGAACCGGAACCTCACTATCCGCAGAGTGAGGAAGGAGGACGAAGGCC
TCTACACCTGCCAGGCATGCAGTGTTCTTGGCTGTGCAAAAGTGGAGGCATTTT
TCATAATAGAAGGTGCCCAGGAAAAGACGAACTTGGAAATCATTATTCTAGTAG
GCACGGCGGTGATTGCCATGTTCTTCTGGCTACTTCTTGTCATCATCCTACGGA
CCGTTAAGCGGGCCAATGGAGGGGAACTGAAGACAGGGTACCTGTCCATCGT
```

FIG. 1A

```
CATGGACCCAGATGAACTCCCATTGGATGAACATTGTGAACGACTGCCTTATGA
TGCCAGCAAATGGGAATTCCCCAGAGACCGGCTGAAGCTAGGTAAGCCTCTTG
GCCGTGGTGCCTTTGGCCAAGTGATTGAAGCAGATGCCTTTGGAATTGACAAG
ACAGCAACTTGCAGGACAGTAGCAGTCAAAATGTTGAAAGAAGGAGCAACACA
CAGTGAGCATCGAGCTCTCATGTCTGAACTCAAGATCCTCATTCATATTGGTCA
CCATCTCAATGTGGTCAACCTTCTAGGTGCCTGTACCAAGCCAGGAGGGCCAC
TCATGGTGATTGTGGAATTCTGCAAATTTGGAAACCTGTCCACTTACCTGAGGA
GCAAGAGAAATGAATTTGTCCCCTACAAGACCAAAGGGGCACGATTCCGTCAA
GGGAAAGACTACGTTGGAGCAATCCCTGTGGATCTGAAACGGCGCTTGGACAG
CATCACCAGTAGCCAGAGCTCAGCCAGCTCTGGATTTGTGGAGGAGAAGTCCC
TCAGTGATGTAGAAGAAGAGGAAGCTCCTGAAGATCTGTATAAGGACTTCCTG
ACCTTGGAGCATCTCATCTGTTACAGCTTCCAAGTGGCTAAGGGCATGGAGTTC
TTGGCATCGCGAAAGTGTATCCACAGGGACCTGGCGGCACGAAATATCCTCTT
ATCGGAGAAGAACGTGGTTAAAATCTGTGACTTTGGCTTGGCCCGGGATATTTA
TAAAGATCCAGATTATGTCAGAAAAGGAGATGCTCGCCTCCCTTTGAAATGGAT
GGCCCCAGAAACAATTTTTGACAGAGTGTACACAATCCAGAGTGACGTCTGGT
CTTTTGGTGTTTTGCTGTGGGAAATATTTTCCTTAGGTGCTTCTCCATATCCTGG
GGTAAAGATTGATGAAGAATTTTGTAGGCGATTGAAAGAAGGAACTAGAATGA
GGGCCCCTGATTATACTACACCAGAAATGTACCAGACCATGCTGGACTGCTGG
CACGGGGAGCCCAGTCAGAGACCCACGTTTTCAGAGTTGGTGGAACATTTGGG
AAATCTCTTGCAAGCTAATGCTCAGCAGGATGGCAAAGACTACATTGTTCTTCC
GATATCAGAGACTTTGAGCATGGAAGAGGATTCTGGACTCTCTCTGCCTACCTC
ACCTGTTTCCTGTATGGAGGAGGAGGAAGTATGTGACCCCAAATTCCATTATGA
CAACACAGCAGGAATCAGTCAGTATCTGCAGAACAGTAAGCGAAAGAGCCGGC
CTGTGAGTGTAAAAACATTTGAAGATATCCCGTTAGAAGAACCAGAAGTAAAAG
TAATCCCAGATGACAACCAGACGGACAGTGGTATGGTTCTTGCCTCAGAAGAG
CTGAAAACTTTGGAAGACAGAACCAAATTATCTCCATCTTTTGGTGGAATGGTG
CCCAGCAAAAGCAGGGAGTCTGTGGCATCTGAAGGCTCAAACCAGACAAGCG
GCTACCAGTCCGGATATCACTCCGATGACACAGACACCACCGTGTACTCCAGT
GAGGAAGCAGAACTTTTAAAGCTGATAGAGATTGGAGTGCAAACCGGTAGCAC
AGCCCAGATTCTCCAGCCTGACTCGGGGACCACACTGAGCTCTCCTCCTGTTTA
A (SEQ ID NO:1)
```

FIG. 1B

```
MESKVLLAVALWLCVETRAASVGLPSVSLDLPRLSIQKDILTIKANTTLQTTCRGQR
DLDWLWPNNQSGSEQRVEVTECSDGLFCKTLTIPKVIGNDTGAYKCFYRETDLAS
VIYVYVQDYRSPFIASVSDQHGVVYIIENKNKTVVIPCLGSISNLNVSLCARYPEKR
FVPDGNRISWDSKKGFIIPSYMISYAGMVFCEAKINDESYQSIMYIVVVVGYRIYDV
VLSPSHGIELSVGEKLVLNCTARTELNVGIDFNWEYPSSKHQHKKLVNRDLKTQS
GSEMKKFLSTLTIDGVTRSDQGLYTCAASSGLMTKKNSTFVRVHEKPFVAFGSGM
ESLVEATVGERVRIPAKYLGYPPPEIKWYKNGIPLESNHTIKAGHVLTIMEVSERDT
GNYTVILTNPISKEKQSHVVSLVVYVPPQIGEKSLISPVDSYQYGTTQTLTCTVYAIP
PPHHIHWYWQLEEECANEPSQAVSVTNPYPCEEWRSVEDFQGGNKIEVNKNQFA
LIEGKNKTVSTLVLQAANVSALYKCEAVNKVGRGERVISFHVTRGPETTLQPDMQP
TEQESVSLWCTADRSTFENLTWYKLGPQPLPIHVGELPTPVCKNLDTLWKLNATM
FSNSTNDILIMELKNASLQDQGDTVCLAQDRKTKKRHCVVRQLTVLERVAPTTTGN
LENQTTSIGESIEVSCTASGNPPPQIMWFKDNETLVEDSGIVLKDGNRNLTIRRVRK
EDEGLYTCQACSVLGCAKVEAFFIIEGAQEKTNLEIIILVGTAVIAMFFWLLLVIILRT
VKRANGGELKTGYLSIVMDPDELPLDEHCERLPYDASKWEFPRDRLKLGKPLGRG
AFGQVIEADAFGIDKTATCRTVAVKMLKEGATHSEHRALMSELKILIHIGHHLNVV
NLLGACTKPGGPLMVIVEFCKFGNLSTYLRSKRNEFVPYKTKGARFRQGKDYVG
AIPVDLKRRLDSITSSQSSASSGFVEEKSLSDVEEEEAPEDLYKDFLTLEHLICYSFQ
VAKGMEFLASRKCIHRDLAARNILLSEKNVVKICDFGLARDIYKDPDYVRKGDAR
LPLKWMAPETIFDRVYTIQSDVWSFGVLLWEIFSLGASPYPGVKIDEEFCRRLKEGT
RMRAPDYTTPEMYQTMLDCWHGEPSQRPTFFSELVEHLGNLLQANAQQDGKDYIVL
PISETLSMEEDSGLSLPTSPVSCMEEEEVCDPKFHYDNTAGISQYLQNSKRKSRPVS
VKTFEDIPLEEPEVKVIPDDNQTDSGMVLASEELKTLEDRTKLSPSFGGMVPSKSRE
SVASEGSNQTSGYQSGYHSDDTDTTVYSSEEAELLKLIEIGVQTGSTAQILQPDSGT
TLSSPPV (SEQ ID NO:2)
```

FIG.2

| Anti-phosphotyrosine | | | | | Anti-KDR | | |
|---|---|---|---|---|---|---|---|
| E848 | | | V848 | | E848 | V848 | |
| 12 | 12 | 120 | 12 | 12 | 120 | 12 | Enzyme (ng) |
| − | + | + | − | + | − | − | ATP (1 mM) | kDa
— 121

— 78

SEQUENCE LISTING

<160> NUMBER OF SEQ ID NOS: 8

<210> SEQ ID NO 1
<211> LENGTH: 4071
<212> TYPE: DNA
<213> ORGANISM: Human

<400> SEQUENCE: 1

```
atggagagca aggtgctgct ggccgtcgcc ctgtggctct gcgtggagac ccgggccgcc      60
tctgtgggtt tgcctagtgt ttctcttgat ctgcccaggc tcagcataca aaaagacata     120
cttacaatta aggctaatac aactcttcaa attacttgca ggggacagag ggacttggac     180
tggctttggc ccaataatca gagtggcagt gagcaaaggg tggaggtgac tgagtgcagc     240
gatggcctct tctgtaagac actcacaatt ccaaaagtga tcggaaatga cactggagcc     300
tacaagtgct tctaccggga aactgacttg gcctcggtca tttatgtcta tgttcaagat     360
tacagatctc catttattgc ttctgttagt gaccaacatg gagtcgtgta cattactgag     420
aacaaaaaca aaactgtggt gattccatgt ctcgggtcca tttcaaatct caacgtgtca     480
ctttgtgcaa gatacccaga aaagagattt gttcctgatg taacagaat ttcctgggac     540 agcaagaagg gctttactat tcccagctac atgatcagct atgctggcat ggtcttctgt     600
gaagcaaaaa ttaatgatga aagttaccag tctattatgt acatagttgt cgttgtaggg     660
tataggattt atgatgtggt tctgagtccg tctcatggaa ttgaactatc tgttggagaa     720
aagcttgtct taaattgtac agcaagaact gaactaaatg tggggattga cttcaactgg     780
gaatacccct tcgaagca tcagcataag aaacttgtaa accgagacct aaaaacccag     840
tctgggagtg agatgaagaa atttttgagc accttaacta tagatggtgt aacccggagt     900
```

```
gaccaaggat tgtacacctg tgcagcatcc agtgggctga tgaccaagaa gaacagcaca      960
tttgtcaggg tccatgaaaa accttttgtt gcttttggaa gtggcatgga atctctggtg     1020
gaagccacgg tgggggagcg tgtcagaatc cctgcgaagt accttggtta cccaccccca     1080
gaaataaaat ggtataaaaa tggaataccc cttgagtcca atcacacaat taaagcgggg     1140
catgtactga cgattatgga agtgagtgaa agagacacag gaaattacac tgtcatcctt     1200
accaatccca tttcaaagga gaagcagagc catgtggtct ctctggttgt gtatgtccca     1260
ccccagattg gtgagaaatc tctaatctct cctgtggatt cctaccagta cggcaccact     1320
caaacgctga catgtacggt ctatgccatt cctcccccgc atcacatcca ctggtattgg     1380
cagttggagg aagagtgcgc caacgagccc agccaagctg tctcagtgac aaacccatac     1440
ccttgtgaag aatggagaag tgtggaggac ttccagggag gaaataaaat tgaagttaat     1500
aaaaatcaat ttgctctaat tgaaggaaaa acaaaactg taagtaccct tgttatccaa      1560
gcggcaaatg tgtcagcttt gtacaaatgt gaagcggtca acaaagtcgg gagaggagag     1620
agggtgatct ccttccacgt gaccaggggg cctgaaatta cttttgcaacc tgacatgcag    1680 cccactgagc aggagagcgt gtcttttgtgg tgcactgcag acagatctac gtttgagaac    1740
ctcacatggt acaagcttgg cccacagcct ctgccaatcc atgtgggaga gttgcccaca    1800 cctgttttgca agaacttgga tactctttgg aaattgaatg ccaccatgtt ctctaatagc     1860
acaaatgaca ttttgatcat ggagcttaag aatgcatcct tgcaggacca aggagactat     1920
gtctgccttg ctcaagacag gaagaccaag aaaagacatt gcgtggtcag gcagctcaca     1980
gtcctagagc gtgtggcacc cacgatcaca ggaaacctgg agaatcagac gacaagtatt     2040
ggggaaagca tcgaagtctc atgcacggca tctgggaatc cccctccaca gatcatgtgg     2100
tttaaagata tgagaccct tgtagaagac tcaggcattg tattgaagga tgggaaccgg     2160
aacctcacta tccgcagagt gaggaaggag gacgaaggcc tctacacctg ccaggcatgc     2220
agtgttcttg gctgtgcaaa agtggaggca tttttcataa tagaaggtgc ccaggaaaag     2280
acgaacttgg aaatcattat tctagtaggc acggcggtga ttgccatgtt cttctggcta     2340
cttcttgtca tcatcctacg gaccgttaag cgggccaatg gagggaact gaagacaggg     2400 tacctgtcca tcgtcatgga tccagatgaa ctcccattgg atgaacattg tgaacgactg     2460
ccttatgatg ccagcaaatg ggaattcccc agagaccggc tgaagctagg taagcctctt     2520
ggccgtggtg cctttggcca agtgattgaa gcagatgcct ttggaattga caagacagca     2580
acttgcagga cagtagcagt caaaatgttg aaagaaggag caacacacag tgagcatcga     2640
gctctcatgt ctgaactcaa gatcctcatt catattggtc accatctcaa tgtggtcaac     2700
cttctaggtg cctgtaccaa gccaggaggg ccactcatgg tgattgtgga attctgcaaa     2760
tttggaaacc tgtccactta cctgaggagc aagagaaatg aatttgtccc ctacaagacc     2820 aaagggcac gattccgtca agggaaagac tacgttggag caatccctgt ggatctgaaa     2880
cggcgcttgg acagcatcac cagtagccag agctcagcca gctctggatt tgtggaggag     2940
aagtccctca gtgatgtaga agaagaggaa gctcctgaag atctgtataa ggacttcctg     3000
accttggagc atctcatctg ttacagcttc caagtggcta agggcatgga gttcttggca     3060
tcgcgaaagt gtatccacag ggacctggcg gcacgaaata tcctcttatc ggagaagaac     3120
gtggttaaaa tctgtgactt tggcttggcc cgggatattt ataaagatcc agattatgtc     3180
agaaaaggag atgctcgcct ccctttgaaa tggatggccc cagaaacaat ttttgacaga     3240
```

-continued

```
gtgtacacaa tccagagtga cgtctggtct tttggtgttt tgctgtggga aatattttcc     3300
ttaggtgctt ctccatatcc tggggtaaag attgatgaag aattttgtag gcgattgaaa     3360
gaaggaacta gaatgagggc ccctgattat actacaccag aaatgtacca gaccatgctg     3420
gactgctggc acggggagcc cagtcagaga cccacgtttt cagagttggt ggaacatttg     3480
ggaaatctct tgcaagctaa tgctcagcag gatggcaaag actacattgt tcttccgata     3540
tcagagactt tgagcatgga agaggattct ggactctctc tgcctacctc acctgtttcc     3600
tgtatggagg aggaggaagt atgtgacccc aaattccatt atgacaacac agcaggaatc     3660
agtcagtatc tgcagaacag taagcgaaag agccggcctg tgagtgtaaa acatttgaa      3720 gatatcccgt tagaagaacc agaagtaaaa gtaatcccag atgacaacca gacggacagt     3780
ggtatggttc ttgcctcaga agagctgaaa actttggaag acagaaccaa attatctcca     3840
tcttttggtg gaatggtgcc cagcaaaagc agggagtctg tggcatctga aggctcaaac     3900
cagacaagcg gctaccagtc cggatatcac tccgatgaca cagacaccac cgtgtactcc     3960
agtgaggaag cagaactttt aaagctgata gagattggag tgcaaaccgg tagcacagcc     4020
cagattctcc agcctgactc ggggaccaca ctgagctctc tcctgtttta a              4071
```

<210> SEQ ID NO 2
<211> LENGTH: 1356
<212> TYPE: PRT
<213> ORGANISM: Human

<400> SEQUENCE: 2

```
Met Glu Ser Lys Val Leu Leu Ala Val Ala Leu Trp Leu Cys Val Glu
 1               5                  10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
```

-continued

```
225                 230                 235                 240
Lys Leu Val Leu Asn Cys Thr Ala Arg Thr Glu Leu Asn Val Gly Ile
                245                 250                 255
Asp Phe Asn Trp Glu Tyr Pro Ser Ser Lys His Gln His Lys Lys Leu
                260                 265                 270
Val Asn Arg Asp Leu Lys Thr Gln Ser Gly Ser Glu Met Lys Lys Phe
            275                 280                 285
Leu Ser Thr Leu Thr Ile Asp Gly Val Thr Arg Ser Asp Gln Gly Leu
        290                 295                 300
Tyr Thr Cys Ala Ala Ser Ser Gly Leu Met Thr Lys Lys Asn Ser Thr
305                 310                 315                 320
Phe Val Arg Val His Glu Lys Pro Phe Val Ala Phe Gly Ser Gly Met
                325                 330                 335
Glu Ser Leu Val Glu Ala Thr Val Gly Glu Arg Val Arg Ile Pro Ala
                340                 345                 350
Lys Tyr Leu Gly Tyr Pro Pro Pro Glu Ile Lys Trp Tyr Lys Asn Gly
            355                 360                 365
Ile Pro Leu Glu Ser Asn His Thr Ile Lys Ala Gly His Val Leu Thr
        370                 375                 380
Ile Met Glu Val Ser Glu Arg Asp Thr Gly Asn Tyr Thr Val Ile Leu
385                 390                 395                 400
Thr Asn Pro Ile Ser Lys Glu Lys Gln Ser His Val Val Ser Leu Val
                405                 410                 415
Val Tyr Val Pro Pro Gln Ile Gly Glu Lys Ser Leu Ile Ser Pro Val
                420                 425                 430
Asp Ser Tyr Gln Tyr Gly Thr Thr Gln Thr Leu Thr Cys Thr Val Tyr
            435                 440                 445
Ala Ile Pro Pro Pro His His Ile His Trp Tyr Trp Gln Leu Glu Glu
        450                 455                 460
Glu Cys Ala Asn Glu Pro Ser Gln Ala Val Ser Val Thr Asn Pro Tyr
465                 470                 475                 480
Pro Cys Glu Glu Trp Arg Ser Val Glu Asp Phe Gln Gly Gly Asn Lys
                485                 490                 495
Ile Glu Val Asn Lys Asn Gln Phe Ala Leu Ile Glu Gly Lys Asn Lys
                500                 505                 510
Thr Val Ser Thr Leu Val Ile Gln Ala Ala Asn Val Ser Ala Leu Tyr
            515                 520                 525
Lys Cys Glu Ala Val Asn Lys Val Gly Arg Gly Glu Arg Val Ile Ser
        530                 535                 540
Phe His Val Thr Arg Gly Pro Glu Ile Thr Leu Gln Pro Asp Met Gln
545                 550                 555                 560
Pro Thr Glu Gln Glu Ser Val Ser Leu Trp Cys Thr Ala Asp Arg Ser
                565                 570                 575
Thr Phe Glu Asn Leu Thr Trp Tyr Lys Leu Gly Pro Gln Pro Leu Pro
                580                 585                 590
Ile His Val Gly Glu Leu Pro Thr Pro Val Cys Lys Asn Leu Asp Thr
            595                 600                 605
Leu Trp Lys Leu Asn Ala Thr Met Phe Ser Asn Ser Thr Asn Asp Ile
        610                 615                 620
Leu Ile Met Glu Leu Lys Asn Ala Ser Leu Gln Asp Gln Gly Asp Tyr
625                 630                 635                 640
Val Cys Leu Ala Gln Asp Arg Lys Thr Lys Lys Arg His Cys Val Val
                645                 650                 655
```

-continued

```
Arg Gln Leu Thr Val Leu Glu Arg Val Ala Pro Thr Ile Thr Gly Asn
            660                 665                 670
Leu Glu Asn Gln Thr Thr Ser Ile Gly Glu Ser Ile Glu Val Ser Cys
        675                 680                 685
Thr Ala Ser Gly Asn Pro Pro Pro Gln Ile Met Trp Phe Lys Asp Asn
        690                 695                 700
Glu Thr Leu Val Glu Asp Ser Gly Ile Val Leu Lys Asp Gly Asn Arg
705                 710                 715                 720
Asn Leu Thr Ile Arg Arg Val Arg Lys Glu Asp Glu Gly Leu Tyr Thr
                725                 730                 735
Cys Gln Ala Cys Ser Val Leu Gly Cys Ala Lys Val Glu Ala Phe Phe
            740                 745                 750
Ile Ile Glu Gly Ala Gln Glu Lys Thr Asn Leu Glu Ile Ile Ile Leu
        755                 760                 765
Val Gly Thr Ala Val Ile Ala Met Phe Phe Trp Leu Leu Leu Val Ile
        770                 775                 780
Ile Leu Arg Thr Val Lys Arg Ala Asn Gly Gly Glu Leu Lys Thr Gly
785                 790                 795                 800
Tyr Leu Ser Ile Val Met Asp Pro Asp Glu Leu Pro Leu Asp Glu His
                805                 810                 815
Cys Glu Arg Leu Pro Tyr Asp Ala Ser Lys Trp Glu Phe Pro Arg Asp
            820                 825                 830
Arg Leu Lys Leu Gly Lys Pro Leu Gly Arg Gly Ala Phe Gly Gln Val
        835                 840                 845
Ile Glu Ala Asp Ala Phe Gly Ile Asp Lys Thr Ala Thr Cys Arg Thr
        850                 855                 860
Val Ala Val Lys Met Leu Lys Glu Gly Ala Thr His Ser Glu His Arg
865                 870                 875                 880
Ala Leu Met Ser Glu Leu Lys Ile Leu Ile His Ile Gly His His Leu
                885                 890                 895
Asn Val Val Asn Leu Leu Gly Ala Cys Thr Lys Pro Gly Gly Pro Leu
            900                 905                 910
Met Val Ile Val Glu Phe Cys Lys Phe Gly Asn Leu Ser Thr Tyr Leu
        915                 920                 925
Arg Ser Lys Arg Asn Glu Phe Val Pro Tyr Lys Thr Lys Gly Ala Arg
        930                 935                 940
Phe Arg Gln Gly Lys Asp Tyr Val Gly Ala Ile Pro Val Asp Leu Lys
945                 950                 955                 960
Arg Arg Leu Asp Ser Ile Thr Ser Ser Gln Ser Ser Ala Ser Ser Gly
                965                 970                 975
Phe Val Glu Glu Lys Ser Leu Ser Asp Val Glu Glu Glu Glu Ala Pro
            980                 985                 990
Glu Asp Leu Tyr Lys Asp Phe Leu Thr Leu Glu His Leu Ile Cys Tyr
        995                 1000                1005
Ser Phe Gln Val Ala Lys Gly Met Glu Phe Leu Ala Ser Arg Lys Cys
    1010                1015                1020
Ile His Arg Asp Leu Ala Ala Arg Asn Ile Leu Leu Ser Glu Lys Asn
1025                1030                1035                1040
Val Val Lys Ile Cys Asp Phe Gly Leu Ala Arg Asp Ile Tyr Lys Asp
                1045                1050                1055
Pro Asp Tyr Val Arg Lys Gly Asp Ala Arg Leu Pro Leu Lys Trp Met
            1060                1065                1070
```

-continued

```
Ala Pro Glu Thr Ile Phe Asp Arg Val Tyr Thr Ile Gln Ser Asp Val
        1075                1080                1085
Trp Ser Phe Gly Val Leu Leu Trp Glu Ile Phe Ser Leu Gly Ala Ser
        1090                1095                1100
Pro Tyr Pro Gly Val Lys Ile Asp Glu Glu Phe Cys Arg Arg Leu Lys
1105                1110                1115                1120
Glu Gly Thr Arg Met Arg Ala Pro Asp Tyr Thr Thr Pro Glu Met Tyr
                1125                1130                1135
Gln Thr Met Leu Asp Cys Trp His Gly Glu Pro Ser Gln Arg Pro Thr
        1140                1145                1150
Phe Ser Glu Leu Val Glu His Leu Gly Asn Leu Leu Gln Ala Asn Ala
        1155                1160                1165
Gln Gln Asp Gly Lys Asp Tyr Ile Val Leu Pro Ile Ser Glu Thr Leu
        1170                1175                1180
Ser Met Glu Glu Asp Ser Gly Leu Ser Leu Pro Thr Ser Pro Val Ser
1185                1190                1195                1200
Cys Met Glu Glu Glu Val Cys Asp Pro Lys Phe His Tyr Asp Asn
                1205                1210                1215
Thr Ala Gly Ile Ser Gln Tyr Leu Gln Asn Ser Lys Arg Lys Ser Arg
        1220                1225                1230
Pro Val Ser Val Lys Thr Phe Glu Asp Ile Pro Leu Glu Glu Pro Glu
        1235                1240                1245
Val Lys Val Ile Pro Asp Asp Asn Gln Thr Asp Ser Gly Met Val Leu
1250                1255                1260
Ala Ser Glu Glu Leu Lys Thr Leu Glu Asp Arg Thr Lys Leu Ser Pro
1265                1270                1275                1280
Ser Phe Gly Gly Met Val Pro Ser Lys Ser Arg Glu Ser Val Ala Ser
                1285                1290                1295
Glu Gly Ser Asn Gln Thr Ser Gly Tyr Gln Ser Gly Tyr His Ser Asp
                1300                1305                1310
Asp Thr Asp Thr Thr Val Tyr Ser Ser Glu Glu Ala Glu Leu Leu Lys
        1315                1320                1325
Leu Ile Glu Ile Gly Val Gln Thr Gly Ser Thr Ala Gln Ile Leu Gln
        1330                1335                1340
Pro Asp Ser Gly Thr Thr Leu Ser Ser Pro Pro Val
1345                1350                1355

<210> SEQ ID NO 3
<211> LENGTH: 28
<212> TYPE: DNA
<213> ORGANISM: Artificial Sequence
<220> FEATURE:
<223> OTHER INFORMATION: Oligonucleotide

<400> SEQUENCE: 3
ggaattccat ccaagcggca aatgtgtc                                      28

<210> SEQ ID NO 4
<211> LENGTH: 28
<212> TYPE: DNA
<213> ORGANISM: Artificial Sequence
<220> FEATURE:
<223> OTHER INFORMATION: Oligonucleotide

<400> SEQUENCE: 4
ggaattccga gtcttctaca agggtctc                                      28
```

-continued

```
<210> SEQ ID NO 5
<211> LENGTH: 18
<212> TYPE: DNA
<213> ORGANISM: Artificial Sequence
<220> FEATURE:
<223> OTHER INFORMATION: Oligonucleotide

<400> SEQUENCE: 5
ttatgacaac acagcagg                                                 18

<210> SEQ ID NO 6
<211> LENGTH: 28
<212> TYPE: DNA
<213> ORGANISM: Artificial Sequence
<220> FEATURE:
<223> OTHER INFORMATION: Oligonucleotide

<400> SEQUENCE: 6
ttggatcctc gagttggggt gtggatgc                                      28

<210> SEQ ID NO 7
<211> LENGTH: 22
<212> TYPE: DNA
<213> ORGANISM: Artificial Sequence
<220> FEATURE:
<223> OTHER INFORMATION: Oligonucleotide

<400> SEQUENCE: 7
ggatccagat gaactcccat tg                                            22

<210> SEQ ID NO 8
<211> LENGTH: 30
<212> TYPE: DNA
<213> ORGANISM: Artificial Sequence
<220> FEATURE:
<223> OTHER INFORMATION: Oligonucleotide

<400> SEQUENCE: 8
gtcgacttag tctttgccat cctgctgagc                                    30
```

HUMAN RECEPTOR TYROSINE KINASE, KDR

CROSS-REFERENCE TO RELATED APPLICATIONS

This application is a division of application Ser. No. 09/483,539, filed Jan. 14, 2000, now U.S. Pat. No. 6,359,115, which is a division of application Ser. No. 09/098,707, filed Jun. 17, 1998, now U.S. Pat. No. 6,204,011, which claims the benefit under 35 U.S.C. §119(e) of U.S. Provisional Application Ser. No. 60/050,962, filed Jun. 18, 1997.

STATEMENT REGARDING FEDERALLY-SPONSORED R&D

Not applicable

REFERENCE TO MICROFICHE APPENDIX

Not applicable

1. Field of the Invention

The present invention relates to an isolated nucleic acid molecule (polynucleotide) which encodes a human receptor tyrosine kinase, KDR, which is expressed on human endothelial cells. This receptor is activated by VEGF and mediates a mitogenic signal. The present invention also relates to recombinant vectors and recombinant hosts which contain a DNA fragment encoding human KDR, a DNA fragment encoding the intracellular portion of KDR, a DNA fragment encoding the extracellular portion of KDR with or without a membrane anchor sequence, substantially purified forms of associated human KDR, and human mutant forms of KDR.

2. Background of the Invention

Vascular endothelial cells form a luminal non-thrombogenic monolayer throughout the vascular system. Mitogens promote embryonic vascular development, growth, repair and angiogenesis in these cells. Angiogenesis involves the proteolytic degradation of the basement membrane on which endothelial cells reside followed by the subsequent chemotactic migration and mitosis of these cells to support sustained growth of a new capillary shoot. One class of mitogens selective for vascular endothelial cells include vascular endothelial growth factor (referred to as VEGF or VEGF-A) and the homologues placenta growth factor (PlGF), VEGF-B and VEGF-C.

Human VEGF exists as a glycosylated homodimer in one of four mature processed forms containing 206, 189 (see U.S. Pat. No. 5,240,848), 165 (see U.S. Pat. No. 5,332,671), and 121 (U.S. Pat. No. 5,332,671) amino acids, the most prevalent being the 165 amino acid form. The 206 amino acid and 189 amino acid forms of human VEGF each contain a highly basic 24-amino acid insert that promotes tight binding to heparin, and presumably, heparin proteoglycans on cellular surfaces and within extracellular matrices (Ferrara et al., 1991, *J. Cell. Biochem.* 47: 211–218).

Human PlGF is also a glycosylated homodimer which shares 46% homology with VEGF at the protein level. Differential splicing of human PlGF mRNA leads to either a 170 or 149 amino acid residue precursor, which are proteolytically processed to mature forms of 152 or 131 amino acid residues in length, respectively (Maglione et al., 1993, *Oncogene* 8: 925–931; Bayne and Thomas, 1992, EPO Publication No. 0 506 477 A1; Hauser and Weich, 1993, *Growth Factors* 9: 259–268).

VEGF-B has been isolated and characterized (Grimmond et al., 1996, *Genome Research* 6: 124–131; Olofsson et al., 1996, *Proc. Natl. Acad. Sci. USA* 93: 2576–2581). The full-length human cDNAs encode 188 and 207 amino acid residue precursors wherein the $NH_2$ terminal portions are proteolytically processed to mature forms 167 and 186 amino acid residues in length. Human VEGF-B expression was found predominantly in heart and skeletal muscle as a disulfide-linked homodimer. However, human VEGF-B may also form a heterodimer with VEGF (id. @ 2580).

VEGF-C has also been isolated and characterized (Joukov et al., 1996, *EMBO J.* 15: 290–298). A cDNA encoding VEGF-C was obtained from a human prostatic adenocarcinoma cell line. A 32 kDa precursor protein is proteolytically processed to generate the mature 23 kDa form, which binds the receptor tyrosine kinase, Flt-4.

VEGF and its homologues impart activity by binding to vascular endothelial cell plasma membrane-spanning tyrosine kinase receptors which then activate an intracellular mitogenic signal. The KDR receptor family is the major tyrosine kinase receptor which transduces the mitogenic signal initiated by VEGF.

Shibuya et al. (1990, *Oncogene* 5: 519–524) disclose a human receptor type tyrosine kinase gene flt, which comprises a 4.2 Kb open reading frame encoding a 1338 amino acid protein which comprises a glycosylated extracelluar domain, membrane spanning region and predicted tyrosine kinase domain.

Pajusola et al. (1992, *Cancer Res.* 52: 5738–5743) disclose a human receptor type tyrosine kinase gene which, as noted above, binds human VEGF-C.

Vascular endothelial growth factor (VEGF) binds the high affinity membrane-spanning tyrosine kinase receptors KDR and Flt-1. Cell culture and gene knockout experiments indicate that each receptor contributes to different aspects of angiogenesis. KDR mediates the mitogenic function of VEGF whereas Flt-1 appears to modulate non-mitogenic functions such as those associated with cellular adhesion. Inhibiting KDR thus significantly diminishes the level of mitogenic VEGF activity.

Vascular growth in the retina leads to visual degeneration culminating in blindness. VEGF accounts for most of the angiogenic activity produced in or near the retina in diabetic retinopathy. Ocular VEGF mRNA and protein are elevated by conditions such as retinal vein occlusion in primates and decreased $pO_2$ levels in mice that lead to neovascularization. Intraocular injections of either anti-VEGF mono-clonal antibodies or VEGF receptor immunofusions inhibit ocular neovascularization in rodent and primate models. Regardless of the cause of induction of VEGF in human diabetic retinopathy, inhibition of ocular VEGF is useful in treating the disease.

Expression of VEGF is also significantly increased in hypoxic regions of animal and human tumors adjacent to areas of necrosis. Monoclonal and polyclonal anti-VEGF antibodies inhibit the growth of human tumors in nude mice. Although these same tumor cells continue to express VEGF in culture, the antibodies do not diminish their mitotic rate of most, if not all, tumor cells derived from cells other than vascular endothelial cells themselves. Thus tumor-derived VEGF does not function as an autocrine mitogenic factor for most tumors. Therefore, VEGF contributes to tumor growth in vivo by promoting angiogenesis through its paracrine vascular endothelial cell chemotactic and mitogenic activities. These monoclonal antibodies also inhibit the growth of typically less well vascularized human colon cancers in athymic mice and decrease the number of tumors arising from inoculated cells. Viral expression of a VEGF-binding construct of Flk-1, the mouse KDR receptor homologue, truncated to eliminate the cytoplasmic tyrosine kinase domains but retaining a membrane anchor, virtually abolishes the growth of a transplantable glioblastoma in mice presumably by the dominant negative mechanism of heterodimer formation with membrane-spanning endothelial cell VEGF receptors. Embryonic stem cells, which normally grow as solid tumors in nude mice, do not produce detectable tumors if both VEGF alleles are knocked out. Taken together, these data indicate the role of VEGF in the growth of solid tumors. KDR and Flt-1 are implicated in pathological neoangiogenesis, and inhibitors of these receptors are useful in the treatment of diseases in which neoangiogenesis is part of the overall pathology, e.g., diabetic retinal vascularization, various forms of cancer as well as forms of inflammation such as rheumatoid arthritis, psoriasis, contact dermatitis and hypersensitivity reaction.

Terman et al. (1991, *Oncogene* 6: 1677–1683; 1992, *Biochem. Biophys. Res. Commun.* 187: 1579–1586) disclose a full-length cDNA encoding a form of KDR. However, the Terman et al. disclosures do not identify a novel, optimal nucleic acid fragment encoding the human form of the receptor type tyrosine kinase gene, KDR. It will be advantageous to identify and isolate a human cDNA sequence encoding an optimized form of human KDR. A nucleic acid molecule expressing the human KDR protein will be useful in screening for compounds acting as a modulator of the protein kinase domain of this protein. Such a compound or compounds will be useful in modulating the mitogenic signal of VEGF and VEGF-related proteins on vascular endothelial cells. The KDR nucleic acid sequence may be also useful for gene therapy encoding a portion of the KDR protein that would contain functional ligand binding and membrane anchoring moieties but not tyrosine kinase activity. Either all or a portion of the KDR protein is also useful to screen for VEGF antagonists. The KDR nucleic acid sequence can be transfected into cells for analysis of function in the absence of Flt-1. The KDR protein is also useful for x-ray structure analysis in the presence or absence of ligand and/or inhibitors. The present invention addresses and meets these needs by disclosing an isolated nucleic acid fragment which expresses a form of human KDR which is shown by computer modeling to be predictive of higher activity and functionality than the previously disclosed KDR.

SUMMARY OF THE INVENTION

The present invention relates to an isolated nucleic acid molecule (polynucleotide) which encodes a novel human receptor type tyrosine kinase gene, KDR. This specification discloses a novel, optimized DNA molecule which encodes, KDR, a receptor tyrosine kinase expressed on human endothelial cells.

The present invention also relates to biologically active fragments or mutants of SEQ ID NO:1 which encodes mRNA expressing a novel human receptor type tyrosine kinase gene, KDR. Any such biologically active fragment and/or mutant will encode either a protein or protein fragment comprising at least an intracellular or extracelluar kinase domain similar to that of the human KDR protein as set forth in SEQ ID NO:2. Any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use and would be useful for screening for agonists and/or antagonists for KDR function.

The isolated nucleic acid molecule of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

The present invention also relates to recombinant vectors and recombinant hosts, both prokaryotic and eukaryotic, which contain the substantially purified nucleic acid molecules disclosed throughout this specification.

The present invention also relates to subcellular membrane fractions of the recombinant host cells (both prokaryotic and eukaryotic as well as both stably and transiently transformed cells) comprising the nucleic acids of the present invention. These subcellular membrane fractions will comprise either wild-type or human mutant forms of KDR at levels substantially above wild-type levels and hence will be useful in various assays described throughout this specification.

A preferred aspect of the present invention is disclosed in FIG. 1A and FIG. 1B and SEQ ID NO:1, a human cDNA encoding a novel receptor type tyrosine kinase gene, KDR.

The present invention also relates to a substantially purified form of the receptor type tyrosine kinase gene, KDR which is disclosed in FIG. 2 and as set forth in SEQ ID NO:2.

The present invention; also relates to biologically active fragments and/or mutants of the KDR protein as initially set forth as SEQ ID NO:2, including but not necessarily limited to amino acid substitutions, deletions, additions, amino terminal truncations and carboxy-terminal truncations such that these mutations provide for proteins or protein fragments of diagnostic, therapeutic or prophylactic use and would be useful for screening for agonists and/or antagonists for KDR function.

A preferred aspect of the present invention is disclosed in FIG. 2 and is set forth as SEQ ID NO:2, the amino acid sequence of the novel receptor type tyrosine kinase gene, KDR.

The present invention also relates to polyclonal and monoclonal antibodies raised in response to either the human form of KDR disclosed herein, or a biologically active fragment thereof.

The present invention also relates to isolated nucleic acid molecules which are fusion constructions expressing fusion proteins useful in assays to identify compounds which modulate wild-type human KDR activity. A preferred aspect of this portion of the invention includes, but is not limited to, glutathione S-transferase (GST)-KDR fusion constructs. These fusion constructs include, but are not limited to, either the intracellular tyrosine kinase domain of human KDR as an in-frame fusion at the carboxy terminus of the GST gene or the extracellular ligand binding domain fused to an immunoglobulin gene by methods known to one of ordinary skill in the art. Soluble recombinant GST-kinase domain fusion proteins may be expressed in various expression systems, including *Spodoptera frugiperda* (Sf21) insect cells (Invitrogen) using a baculovirus expression vector (pAcG2T, Pharmingen).

The present invention also relates to isolated nucleic acid molecules which encode human KDR protein fragments comprising a portion of the intracellular KDR domain. The protein fragments are useful in assays to identify compounds which modulate wild-type human KDR activity. A preferred aspect of this portion of the invention includes, but is not limited to, a nucleic acid construction which encodes the intracellular portion of human KDR, from about amino acid 780–795 to about amino acid 1175–1386.

Therefore, the present invention relates to isolated nucleic acid molecules which encode human KDR protein fragments comprising a portion of the extracellular KDR domain. These isolated nucleic acid proteins may or may not include nucleotide sequences which also encode the transmembrane domain of human KDR. These KDR extracellular and/or KDR extracellular-transmembrane domain protein fragments will be useful in screening for compounds which inhibit VEGF binding as well as utilizing these isolated nucleic acids as gene therapy vehicles to inhibit VEGF-mediated mitogenic activity. Expression of either a soluble version of KDR (extracellular) or membrane bound form (extracellular-transmembrane) will inhibit in vivo VEGF/KDR mediated angiogenesis.

Therefore, the present invention relates to methods of expressing the receptor type tyrosine kinase gene, KDR, and biological equivalents disclosed herein, assays employing these receptor type tyrosine kinase genes, cells expressing these receptor type tyrosine kinase genes, and compounds identified through the use of these receptor type tyrosine kinase genes and expressed human KDR protein, including one or more modulators of the human KDR-dependent kinase either through direct contact with the kinase domain of human KDR or a compound which prevents binding of VEGF to human KDR, or appropriate dimerization of the KDR receptor antagonizing transduction of the normal intracellular signals associated with VEGF-induced angiogenesis.

The present invention also relates to gene therapy applications, especially for nucleic acid fragments which encode soluble extracelluar protein fragments of human KDR. It is disclosed herein that such methods will be useful especially in the treatment of various tumors as well as diabetic retinopathy.

It is an object of the present invention to provide an isolated nucleic acid molecule which encodes a novel form of human KDR, or human KDR fragments and KDR mutants which are derivatives of SEQ ID NO:2 and preferably retain Val at position 848, and especially preferable is retention of Val at position 848, Glu at position 498, Ala at position 772, Arg at position 787, Lys at position 835 and Ser at position 1347. Any such polynucleotide includes but is not necessarily limited to nucleotide substitutions, deletions; additions, amino-terminal truncations and carboxy-terminal truncations such that these mutations encode mRNA which express a protein or protein fragment of diagnostic, therapeutic or prophylactic use and would be useful for screening for agonists and/or antagonists for KDR function.

It is a further object of the present invention to provide the human KDR proteins or protein fragments encoded by the nucleic acid molecules referred to in the preceding paragraph.

It is also an object of the present invention to provide biologically active fragments or mutants of human KDR which comprise an intracellular kinase domain similar to that of the human KDR protein as set forth in SEQ ID NO:2, preferably retaining Val at position 848, and especially preferable is retention of Val at position 848, Glu at position 498, Ala at position 772, Arg at position 787, Lys at position 835 and Ser at position 1347.

It is a further object of the present invention to provide recombinant vectors and recombinant host cells which comprise a nucleic acid sequence encoding human KDR or a biological equivalent thereof.

It is an object of the present invention to provide a substantially purified form of the receptor type tyrosine kinase gene, KDR, as set forth in SEQ ID NO:2.

It is an object of the present invention to provide for biologically active fragments and/or mutants of the KDR protein, such as set forth in SEQ ID NO:2, including but not necessarily limited to amino acid substitutions, deletions, additions, amino terminal truncations and carboxy-terminal truncations such that these mutations provide for proteins or protein fragments of diagnostic, therapeutic or prophylactic use.

It is also an object of the present invention to provide for KDR-based in-frame fusion constructions, methods of expressing the receptor type tyrosine kinase gene, KDR, and biological equivalents disclosed herein, related assays, recombinant cells expressing these receptor type tyrosine kinase genes, and agonistic and/or antagonistic compounds identified through the use of these receptor type tyrosine kinase genes and expressed human KDR protein.

As used herein, "VEGF" or "VEFG-A" refers to vascular endothelial growth factor.

As used herein, "KDR" or "FLK-1" refers to kinase insert domain-containing receptor.

As used herein, "FLT-1" refers to fms-like tyrosine kinase receptor.

As used herein, the term "mammalian host" refers to any mammal, including a human being.

BRIEF DESCRIPTION OF THE DRAWINGS

FIG. 1A and FIG. 1B show the nucleotide sequence which encodes human KDR, as set forth in SEQ ID NO:1.

FIG. 2 shows the amino acid sequence of human KDR, as also set forth in SEQ ID NO:2. Underlined amino acid residues represent differences in comparison to a previously disclosed form of human KDR.

DETAILED DESCRIPTION OF THE INVENTION

Figure 3A:
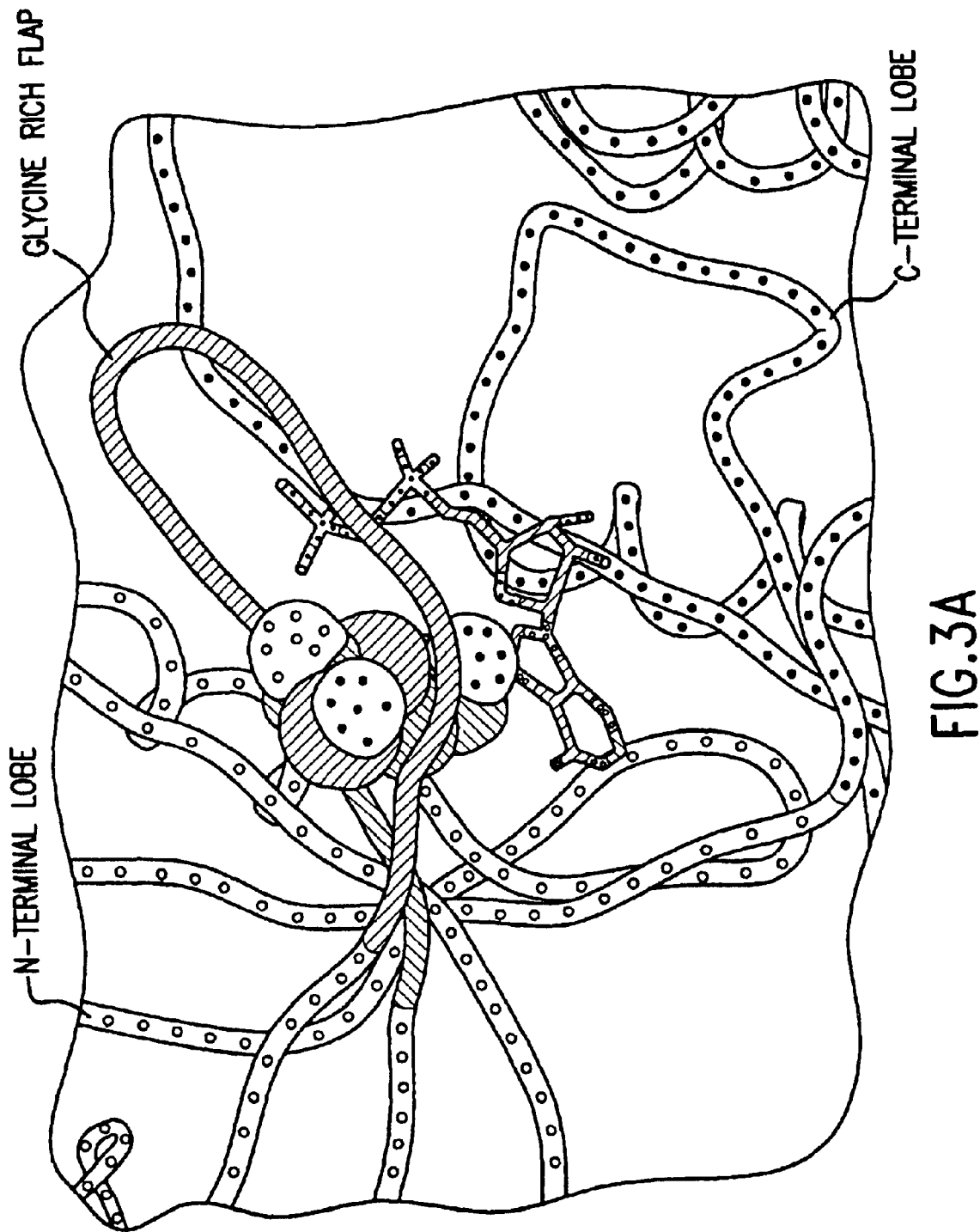
FIG. 3A shows the ATP binding domain from the KDR V848E mutant homology model with bound AMP-PCP. The side chain of E848 is in contact the adenine from AMP-PCP. The gamma phosphate of AMP-PCP is not visible. The protein carbon alpha trace is shown in pipes, the AMP-PCP in sticks and the E848 side chain in space filling. The N-terminal lobe is colored blue (or alternatively labeled with light circles) with the exception of the glycine rich flap which is colored green (or alternatively labeled as a lined region). The C-terminal lobe is colored red (or alternatively labeled with dark circles.

The present invention relates to isolated nucleic acid and protein forms which represent human KDR. This specification discloses a DNA molecule encoding human KDR, a receptor tyrosine kinase expressed on human endothelial cells. The receptor is activated by vascular endothelial growth factor (VEGF) and mediates a mitogenic signal. This activation and subsequent mitogenesis leads to an angiogenic response in vivo. The nucleic acid molecule disclosed in the specification as SEQ ID NO:1 encodes a human KDR protein (SEQ ID NO:2) which results in six amino acid differences from the published sequence (Terman et al., 1992, *Biochem. Biophys. Res. Commun.* 187: 1579–1586, Terman et al., International PCT application number WO 92/14748, International application number PCT/US92/01300). These changes are position 498 (Ala to Glu), 772 (Thr to Ala), 787 (Gly to Arg), 835 (Asn to Lys), 848 (Glu to Val), and 1347 (Thr to Ser). These six amino acid changes affect the activity of the receptor. Val 848 is conserved throughout most of the tyrosine kinase family and appears to be important for the binding of ATP and presumably ATP competitive inhibitors to the KDR receptor kinase as inferred by computer modeling. A change to Glu at this position results in a non-functional kinase as a consequence of impaired ATP binding. The other changes may also cause activity differences.

The present invention also relates to either biologically active fragments or mutants of SEQ ID NO:1 which encodes mRNA expressing a novel human receptor type tyrosine kinase gene, KDR. Any such biologically active fragment and/or mutant will encode a protein or protein fragment comprising at least an intracellular kinase domain similar to that of the human KDR protein as set forth in SEQ ID NO:2 and preferably retain Val at position 848. It is also envisioned that other intracellular-based KDR domains will result in a soluble protein fragment which mimics wild-type intracellular domain structure and function. Any such protein fragment may be a fusion protein, such as the exemplified GST-KDR fusion, or may be solely comprised of the KDR intracelluar domain, with increasing deletions in from the COOH-terminal region. It is especially preferable that the following amino acids be retained, if this domain encompasses the respective protein or protein fragment: Val at position 848, Glu at position 498, Ala at position 772, Arg at position 787, Lys at position 835 and Ser at position 1347. Therefore, any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use and is useful for the identification of modulators of KDR receptor activity.

The isolated nucleic acid molecule of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

It is known that DNA sequences coding for a peptide may be altered so as to code for a peptide having properties that are different than those of the naturally occurring peptide. Methods of altering the DNA sequences include but are not limited to site directed mutagenesis. Examples of altered properties include but are not limited to changes in the affinity of an enzyme for a substrate or a receptor for a ligand.

As used herein, "purified" and "isolated" are utilized interchangeably to stand for the proposition that the nucleic acid, protein, or respective fragment thereof in question has been substantially removed from its in vivo environment so that it may be manipulated by the skilled artisan, such as but not limited to nucleotide sequencing, restriction digestion, site-directed mutagenesis, and subcloning into expression vectors for a nucleic acid fragment as well as obtaining the protein or protein fragment in pure quantities so as to afford the opportunity to generate polyclonal antibodies, monoclonal antibodies, amino acid sequencing, and peptide digestion. Therefore, the nucleic acids claimed herein may be present in whole cells or in cell lysates or in a partially purified or substantially purified form. A nucleic acid is considered substantially purified when it is purified away from environmental contaminants. Thus, a nucleic acid sequence isolated from cells is considered to be substantially purified when purified from cellular components by standard methods while a chemically synthesized nucleic acid sequence is considered to be substantially purified when purified from its chemical precursors.

The present invention also relates to recombinant vectors and recombinant hosts, both prokaryotic and eukaryotic, which contain the substantially purified nucleic acid molecules disclosed throughout this specification.

The present invention also relates to subcellular membrane fractions of the recombinant host cells (both prokaryotic and eukaryotic as well as both stably and transiently transformed cells) comprising the nucleic acids of the present invention. These subcellular membrane fractions will comprise wild-type or human mutant forms of KDR at levels substantially above wild-type levels and hence will be useful in various assays described throughout this specification.

A preferred aspect of the present invention is disclosed in FIG. 1A and FIG. 1B and SEQ ID NO:1, a human cDNA encoding a novel receptor type tyrosine kinase gene, KDR, disclosed as follows:

```
ATGGAGAGCAAGGTGCTGCTGGCCGTCGCCCTGTGGCTCTGCGTGGAGACCCGGGCCGCCTCTGTGGGT    (SEQ ID NO:1)

TTGCCTAGTGTTTCTCTTGATCTGCCCAGGCTCAGCATACAAAAAGACATACTTACAATTAAGGCTAAT

ACAACTCTTCAAATTACTTGCAGGGGACAGAGGGACTTGGACTGGCTTTGGCCCAATAATCAGAGTGGC

AGTGAGCAAAGGGTGGAGGTGACTGAGTGCAGCGATGGCCTCTTCTGTAAGACACTCACAATTCCAAAA

GTGATCGGAAATGACACTGGAGCCTACAAGTGCTTCTACCGGGAAACTGACTTGGCCTCGGTCATTTAT

GTCTATGTTCAAGATTACAGATCTCCATTTATTGCTTCTGTTAGTGACCAACATGGAGTCGTGTACATT
```

-continued

```
ACTGAGAACAAAAACAAAACTGTGGTGATTCCATGTCTCGGGTCCATTTCAAATCTCAACGTGTCACTT
TGTGCAAGATACCCAGAAAAGAGATTTGTTCCTGATGGTAACAGAATTTCCTGGGACAGCAAGAAGGGC
TTTACTATTCCCAGCTACATGATCAGCTATGCTGGCATGGTCTTCTGTGAAGCAAAAATTAATGATGAA
AGTTACCAGTCTATTATGTACATAGTTGTCGTTGTAGGGTATAGGATTTATGATGTGGTTCTGAGTCCG
TCTCATGGAATTGAACTATCTGTTGGAGAAAAGCTTGTCTTAAATTGTACAGCAAGAACTGAACTAAAT
GTGGGGATTGACTTCAACTGGGAATACCCTTCTTCGAAGCATCAGCATAAGAAACTTGTAAACCGAGAC
CTAAAAACCCAGTCTGGGAGTGAGATGAAGAAATTTTTGAGCACCTTAACTATAGATGGTGTAACCCGG
AGTGACCAAGGATTGTACACCTGTGCAGCATCCAGTGGGCTGATGACCAAGAAGAACAGCACATTTGTC
AGGGTCCATGAAAAACCTTTTGTTGCTTTTGGAAGTGGCATGGAATCTCTGGTGGAAGCCACGGTGGGG
GAGCGTGTCAGAATCCCTGCGAAGTACCTTGGTTACCCACCCCCAGAAATAAAATGGTATAAAAATGGA
ATACCCCTTGAGTCCAATCACACAATTAAAGCGGGGCATGTACTGACGATTATGGAAGTGAGTGAAAGA
GACACAGGAAATTACACTGTCATCCTTACCAATCCCATTTCAAAGGAGAAGCAGAGCCATGTGGTCTCT
CTGGTTGTGTATGTCCCACCCCAGATTGGTGAGAAATCTCTAATCTCTCCTGTGGATTCCTACCAGTAC
GGCACCACTCAAACGCTGACATGTACGGTCTATGCCATTCCTCCCCCGCATCACATCCACTGGTATTGG
CAGTTGGAGGAAGAGTGCGCCAACGAGCCCAGCCAAGCTGTCTCAGTGACAAACCCATACCCTTGTGAA
GAATGGAGAAGTGTGGAGGACTTCCAGGGAGGAAATAAAATTGAAGTTAATAAAAATCAATTTGCTCTA
ATTGAAGGAAAAAACAAAACTGTAAGTACCCTTGTTATCCAAGCGGCAAATGTGTCAGCTTTGTACAAA
TGTGAAGCGGTCAACAAAGTCGGGAGAGGAGAGAGGGTGATCTCCTTCCACGTGACCAGGGGTCCTGAA
ATTACTTTGCAACCTGACATGCAGCCCACTGAGCAGGAGAGCGTGTCTTTGTGGTGCACTGCAGACAGA
TCTACGTTTGAGAACCTCACATGGTACAAGCTTGGCCCACAGCCTCTGCCAATCCATGTGGGAGAGTTG
CCCACACCTGTTTGCAAGAACTTGGATACTCTTTGGAAATTGAATGCCACCATGTTCTCTAATAGCACA
AATGACATTTTGATCATGGAGCTTAAGAATGCATCCTTGCAGGACCAAGGAGACTATGTCTGCCTTGCT
CAAGACAGGAAGACCAAGAAAAGACATTGCGTGGTCAGGCAGCTCACAGTCCTAGAGCGTGTGGCACCC
ACGATCACAGGAAACCTGGAGAATCAGACGACAAGTATTGGGGAAAGCATCGAAGTCTCATGCACGGCA
TCTGGGAATCCCCCTCCACAGATCATGTGGTTTAAAGATAATGAGACCCTTGTAGAAGACTCAGGCATT
GTATTGAAGGATGGGAACCGGAACCTCACTATCCGCAGAGTGAGGAAGGAGGACGAAGGCCTCTACACC
TGCCAGGCATGCAGTGTTCTTGGCTGTGCAAAAGTGGAGGCATTTTTCATAATAGAAGGTGCCCAGGAA
AAGACGAACTTGGAAATCATTATTCTAGTAGGCACGGCGGTGATTGCCATGTTCTTCTGGCTACTTCTT
GTCATCATCCTACGGACCGTTAAGCGGGCCAATGGAGGGGAACTGAAGACAGGCTACTTGTCCATCGTC
ATGGATCCAGATGAACTCCCATTGGATGAACATTGTGAACGACTGCCTTATGATGCCAGCAAATGGGAA
TTCCCCAGAGACCGGCTGAAGCTAGGTAAGCCTCTTGGCCGTGGTGCCTTTGGCCAAGTGATTGAAGCA
GATGCCTTTGGAATTGACAAGACAGCAACTTGCAGGACAGTAGCAGTCAAAATGTTGAAAGAAGGAGCA
ACACACAGTGAGCATCGAGCTCTCATGTCTGAACTCAAGATCCTCATTCATATTGGTCACCATCTCAAT
GTGGTCAACCTTCTAGGTGCCTGTACCAAGCCAGGAGGGCCACTCATGGTGATTGTGGAATTCTGCAAA
TTTGGAAACCTGTCCACTTACCTGAGGAGCAAGAGAAATGAATTTGTCCCCTACAAGACCAAAGGGGCA
CGATTCCGTCAAGGGAAAGACTACGTTGGAGCAATCCCTGTGGATCTGAAACGGCGCTTGGACAGCATC
ACCAGTAGCCAGAGCTCAGCCAGCTCTGGATTTGTGGAGGAGAAGTCCCTCAGTGATGTAGAAGAAGAG
GAAGCTCCTGAAGATCTGTATAAGGACTTCCTGACCTTGGAGCATCTCATCTGTTACAGCTTCCAAGTG
GCTAAGGGCATGGAGTTCTTGGCATCGCGAAAGTGTATCCACAGGGACCTGGCGGCACGAAATATCCTC
TTATCGGAGAAGAACGTGGTTAAAATCTGTGACTTTGGCTTGGCCCGGGATATTTATAAAGATCCAGAT
```

-continued
```
TATGTCAGAAAAGGAGATGCTCGCCTCCCTTTGAAATGGATGGCCCCAGAAACAATTTTTGACAGAGTG

TACACAATCCAGAGTGACGTCTGGTCTTTTGGTGTTTTGCTGTGGGAAATATTTTCCTTAGGTGCTTCT

CCATATCCTGGGGTAAAGATTGATGAAGAATTTTGTAGGCGATTGAAAGAAGGAACTAGAATGAGGGCC

CCTGATTATACTACACCAGAAATGTACCAGACCATGCTGGACTGCTGGCACGGGGAGCCCAGTCAGAGA

CCCACGTTTTCAGAGTTGGTGGAACATTTGGGAAATCTCTTGCAAGCTAATGCTCAGCAGGATGGCAAA

GACTACATTGTTCTTCCGATATCAGAGACTTTGAGCATGGAAGAGGATTCTGGACTCTCTCTGCCTACC

TCACCTGTTTCCTGTATGGAGGAGGAGGAAGTATGTGACCCCAAATTCCATTATGACAACACAGCAGGA

ATCAGTCAGTATCTGCAGAACAGTAAGCGAAAGAGCCGGCCTGTGAGTGTAAAAACATTTGAAGATATC

CCGTTAGAAGAACCAGAAGTAAAAGTAATCCCAGATGACAACCAGACGGACAGTGGTATGGTTCTTGCC

TCAGAAGAGCTGAAAACTTTGGAAGACAGAACCAAATTATCTCCATCTTTTGGTGGAATGGTGCCCAGC

AAAAGCAGGGAGTCTGTGGCATCTGAAGGCTCAAACCAGACAAGCGGCTACCAGTCCGGATATCACTCC

GATGACACAGACACCACCGTGTACTCCAGTGAGGAAGCAGAACTTTTAAAGCTGATAGAGATTGGAGTG

CAAACCGGTAGCACAGCCCAGATTCTCCAGCCTGACTCGGGGACCACACTGAGCTCTCCTCCTGTTTAA.
```

The present invention also relates to a substantially purified form of the receptor type tyrosine kinase gene which comprises the KDR amino acid sequence disclosed in FIG. 2 and as set forth in SEQ ID NO:2, which includes Glu at position 498, Ala at position 772, Arg at position 787, Lys at position 835, Val at position 848 and Ser at position 1347, disclosed as follows:

The present invention also relates to biologically active fragments and/or mutants of the KDR protein as initially set forth as SEQ ID NO:2, including but not necessarily limited to amino acid substitutions, deletions, additions, amino terminal truncations and carboxy-terminal truncations such that these mutations provide for proteins or protein fragments of diagnostic, therapeutic or prophylactic use and

```
MESKVLLAVALWLCVETRAASVGLPSVSLDLPRLSIQKDILTIKANTTLQITCRGQRDLDWLWPNNQSG    (SEQ ID NO:2)

SEQRVEVTECSDGLFCKTLTIPKVIGNDTGAYKCFYRETDLASVIYVYVQDYRSPFIASVSDQHGVVYI

TENKNKTVVIPCLGSISNLNVSLCARYPEKRFVPDGNRISWDSKKGFTIPSYMISYAGMVFCEAKINDE

SYQSIMYIVVVVGYRIYDVVLSPSHGIELSVGEKLVLNCTARTELNVGIDFNWEYPSSKHQHKKLVNRD

LKTQSGSEMKKFLSTLTIDGVTRSDQGLYTCAASSGLMTKKNSTFVRVHEKPFVAFGSGMESLVEATVG

ERVRIPAKYLGYPPPEIKWYKNGIPLESNHTIKAGHVLTIMEVSERDTGNYTVILTNPISKEKQSHVVS

LVVYVPPQIGEKSLISPVDSYQYGTTQTLTCTVYAIPPPHHIHWYWQLEEECANEPSQAVSVTNPYPCE

EWRSVEDFQGGNKIEVNKNQFALIEGKNKTVSTLVIQAANVSALYKCEAVNKVGRGERVISFHVTRGPE

ITLQPDMQPTEQESVSLWCTADRSTFENLTWYKLGPQPLPIHVGELPTPVCKNLDTLWKLNATMFSNST

NDILIMELKNASLQDQGDYVCLAQDRKTKKRHCVVRQLTVLERVAPTITGNLENQTTSIGESIEVSCTA

SGNPPPQIMWFKDNETLVEDSGIVLKDGNRNLTIRRVRKEDEGLYTCQACSVLGCAKVEAFFIIEGAQE

KTNLEIIILVGTAVIAMFFWLLLVIILRTVKRANGGELKTGYLSIVMDPDELPLDEHCERLPYDASKWE

FPRDRLKLGKPLGRGAFGQVIEADAFGIDKTATCRTVAVKMLKEGATHSEHRALMSELKILIHIGHHLN

VVNLLGACTKPGGPLMVIVEFCKFGNLSTYLRSKRNEFVPYKTKGARFRQGKDYVGAIPVDLKRRLDSI

TSSQSSASSGFVEEKSLSDVEEEEAPEDLYKDFLTLEHLICYSFQVAKGMEFLASRKCIHRDLAARNIL

LSEKNVVKICDFGLARDIYKDPDYVRKGDARLPLKWMAPETIFDRVYTIQSDVWSFGVLLWEIFSLGAS

PYPGVKIDEEFCRRLKEGTRMRAPDYTTPEMYQTMLDCWHGEPSQRPTFSELVEHLGNLLQANAQQDGK

DYIVLPISETLSMEEDSGLSLPTSPVSCMEEEEVCDPKFHYDNTAGISQYLQNSKRKSRPVSVKTFEDI

PLEEPEVKVIPDDNQTDSGMVLASEELKTLEDRTKLSPSFGGMVPSKSRESVASEGSNQTSGYQSGYHS

DDTDTTVYSSEEAELLKLIEIGVQTGSTAQILQPDSGTTLSSPPV.
``` would be useful for screening for agonists and/or antagonists for KDR function.

A preferred aspect of the present invention is disclosed in FIG. 2 and is set forth as SEQ ID NO:2, the amino acid sequence of the novel receptor type tyrosine kinase gene, KDR.

The present invention also relates to isolated nucleic acid molecules which are fusion constructions useful in assays to identify compounds which modulate wild-type human KDR activity. A preferred aspect of this portion of the invention includes, but is not limited to, GST-KDR fusion constructs. These fusion constructs comprise the intracellular tyrosine kinase domain of human KDR as an in-frame fusion at the carboxy terminus of the GST gene. Soluble recombinant GST-kinase domain fusion proteins may be expressed in various expression systems, including *Spodoptera frugiperda* (Sf21) insect cells (Invitrogen) using a baculovirus expression vector (pAcG2T, Pharmingen).

The present invention relates to isolated nucleic acid molecules which encode soluble portions of the KDR intracellular or extracellular domain. Especially preferred are nucleic acid molecules which encode a COOH-terminal deletion KDR protein fragment useful in assays to identify compounds which modulate wild-type human KDR activity. Any such nucleic acid will encode a KDR protein fragment which mimics KDR wild-type activity within the respective domain, such as the kinase domain of human KDR. These expressed soluble protein fragments may or may not contain a portion of the amino-terminal region of human KDR or of a heterologous sequence. These nucleic acids may be expressed in any of a number of expression systems available to the artisan. Any such intracelluar-based KDR construction of the present invention may be utilized in gene therapy applications, such as acting as an soluble agonist or antagonist of kinase activity normally associated with wild type, membrane associated kinase activity.

Therefore, the present invention relates to isolated nucleic acid molecules which encode human KDR protein fragments comprising a portion of the intracellular KDR domain. The protein fragments are useful in assays to identify compounds which modulate wild-type human KDR activity. A preferred aspect of this portion of the invention includes, but is not limited to, a nucleic acid construction which encodes the intracellular portion of human KDR, from about amino acid 780–795 to about amino acid 1175–1386. The data exemplified in Example Section 3 show that COOH terminal deletions of the soluble intracellular portion of KDR exhibit kinase activity.

The present invention also relates to isolated nucleic acid molecules which encode human KDR protein fragments comprising a portion of the extracellular KDR domain. These isolated nucleic acid proteins may or may not include nucleotide sequences which also encode the transmembrane domain of human KDR. These KDR extracellular and/or KDR extracellular-transmembrane domain protein fragments will be useful in screening for compounds which inhibit VEGF binding as well as utilizing these isolated nucleic acids as gene therapy vehicles to inhibit VEGF-mediated mitogenic activity. Expression of wither a soluble version of KDR (extracellular) or membrane bound form (extracellular-transmembrane) will inhibit VEGF/KDR mediated angiogenesis. A preferred aspect of this portion of the invention includes, but is not limited to, an isolated nucleic acid molecule which encodes at least six of the IG-like extracellular domains from the amino-terminal end of KDR. Such a protein fragment would comprise at least from about the initiating methionine to about amino acid 644 of human KDR (SEQ ID NO:2). Another preferred aspect of this portion of the invention includes, but is not limited to, an isolated nucleic acid molecule which encodes the all seven IG-like extracellular domains from the amino-terminal end of KDR. Such a protein fragment would comprise at least from about the initiating methionine to about amino acid 763. An additional preferred embodiment includes but is not limited to an extracellular-transmembrane construct which encodes about the initial 785–795 amino acids of KDR as set forth in SEQ ID NO:2, and especially preferred is an isolated nucleic acid molecule construction which encodes the amino terminal portion of KDR with a truncation at about amino acid 791 as set forth in SEQ ID NO:2.

Therefore, the present invention relates to methods of expressing the receptor type tyrosine kinase gene, KDR, and biological equivalents disclosed herein, assays employing these receptor type tyrosine kinase genes, cells expressing these receptor type tyrosine kinase genes, and agonistic and/or antagonistic compounds identified through the use of these receptor type tyrosine kinase genes and expressed human KDR protein, including, but not limited to, one or more modulators of the human KDR-dependent kinase either through direct contact with the kinase domain of human KDR or a compound which prevents binding of VEGF to human KDR, or either prevents or promotes receptor dimerization and/or activation thereby either inducing or antagonizing transduction of the normal intracellular signals associated with VEGF-induced angiogenesis As used herein, a "biologically active equivalent" or "functional derivative" of a wild-type human KDR possesses a biological activity that is substantially similar to the biological activity of the wild type human KDR. The term "functional derivative" is intended to include the "fragments," "mutants," "variants," "degenerate variants," "analogs" and "homologues" or to "chemical derivatives" of the wild type human KDR protein. The term "fragment" is meant to refer to any polypeptide subset of wild-type human KDR. The term "mutant" is meant to refer to a molecule that may be substantially similar to the wild-type form but possesses distinguishing biological characteristics. Such altered characteristics include but are in no way limited to altered substrate binding, altered substrate affinity and altered sensitivity to chemical compounds affecting biological activity of the human KDR or human KDR functional derivative. The term "variant" is meant to refer to a molecule substantially similar in structure and function to either the entire wild-type protein or to a fragment thereof. A molecule is "substantially similar" to a wild-type human KDR-like protein if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the full-length human KDR protein or to a biologically active fragment thereof.

Any of a variety of procedures may be used to clone human KDR. These methods include, but are not limited to, (1) a RACE PCR cloning technique (Frohman, et al., 1988, *Proc. Natl. Acad. Sci. USA* 85: 8998–9002). 5' and/or 3' RACE may be performed to generate a full-length cDNA sequence. This strategy involves using gene-specific oligonucleotide primers for PCR amplification of human KDR cDNA. These gene-specific primers are designed through identification of an expressed sequence tag (EST) nucleotide sequence which has been identified by searching any number of publicly available nucleic acid and protein databases; (2) direct functional expression of the human KDR cDNA following the construction of a human KDR-containing cDNA library in an appropriate expression vector system; (3) screening a human KDR-containing cDNA library constructed in a bacteriophage or plasmid shuttle vector with a labeled degenerate oligonucleotide probe designed from the amino acid sequence of the human KDR protein; and (4) screening a human KDR-containing cDNA library constructed in a bacteriophage or plasmid shuttle vector with a partial cDNA encoding the human KDR protein. This partial cDNA is obtained by the specific PCR amplification of human KDR DNA fragments through the design of degenerate oligonucleotide primers from the amino acid sequence known for other kinases which are related to the human KDR protein; (5) screening a human KDR-containing cDNA library constructed in a bacteriophage or plasmid shuttle vector with a partial cDNA encoding the human KDR protein. This strategy may also involve using gene-specific oligonucleotide primers for PCR amplification of human KDR cDNA identified as an EST as described above; or (6) designing 5' and 3' gene specific oligonucleotides using SEQ ID NO: 1 as a template so that either the full-length cDNA may be generated by known RACE techniques, or a portion of the coding region may be generated by these same known RACE techniques to generate and isolate a portion of the coding region to use as a probe to screen one of numerous types of cDNA and/or genomic libraries in order to isolate a full-length version of the nucleotide sequence encoding human KDR.

It is readily apparent to those skilled in the art that other types of libraries, as well as libraries constructed from other cell types- or species types, may be useful for isolating a human KDR-encoding DNA or a human KDR homologue. Other types of libraries include, but are not limited to, cDNA libraries derived from other cells or cell lines other than human cells or tissue such as murine cells, rodent cells or any other such vertebrate host which may contain human KDR-encoding DNA. Additionally a human KDR gene and homologues may be isolated by oligonucleotide- or polynucleotide-based hybridization screening of a vertebrate genomic library, including but not limited to, a murine genomic library, a rodent genomic library, as well as concomitant human genomic DNA libraries.

It is readily apparent to those skilled in the art that suitable cDNA libraries may be prepared from cells or cell lines which have KDR activity. The selection of cells or cell lines for use in preparing a cDNA library to isolate a cDNA encoding human KDR may be done by first measuring cell-associated KDR activity using any known assay available for such a purpose.

Preparation of cDNA libraries can be performed by standard techniques well known in the art. Well known cDNA library construction techniques can be found for example, in Sambrook et al., 1989, *Molecular Cloning: A Laboratory Manual;* Cold Spring Harbor Laboratory, Cold Spring Harbor, N.Y. Complementary DNA libraries may also be obtained from numerous commercial sources, including but not limited to Clontech Laboratories, Inc. and Stratagene.

It is also readily apparent to those skilled in the art that DNA encoding human KDR may also be isolated from a suitable genomic DNA library. Construction of genomic DNA libraries can be performed by standard techniques well known in the art. Well known genomic DNA library construction techniques can be found in Sambrook, et al., supra.

In order to clone the human KDR gene by one of the preferred methods, the amino acid sequence or DNA sequence of human KDR or a homologous protein may be necessary. To accomplish this, the KDR protein or a homologous protein may be purified and partial amino acid sequence determined by automated sequenators. It is not necessary to determine the entire amino acid sequence, but the linear sequence of two regions of 6 to 8 amino acids can be determined for the PCR amplification of a partial human KDR DNA fragment. Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the human KDR sequence but others in the set will be capable of hybridizing to human KDR DNA even in the presence of DNA oligonucleotides with mismatches. The mismatched DNA oligonucleotides may still sufficiently hybridize to the human KDR DNA to permit identification and isolation of human KDR encoding DNA. Alternatively, the nucleotide sequence of a region of an expressed sequence may be identified by searching one or more available genomic databases. Gene-specific primers may be used to perform PCR amplification of a cDNA of interest from either a cDNA library or a population of cDNAs. As noted above, the appropriate nucleotide sequence for use in a PCR-based method may be obtained from SEQ ID NO: 1, either for the purpose of isolating overlapping 5' and 3' RACE products for generation of a full-length sequence coding for human KDR, or to isolate a portion of the nucleotide sequence coding for human KDR for use as a probe to screen one or more cDNA- or genomic-based libraries to isolate a full-length sequence encoding human KDR or human KDR-like proteins.

In an exemplified method, the human KDR full-length cDNA of the present invention was generated by screening a human umbilical vein endothelial cell (HUVEC) lambda phage cDNA library with a KDR-specific 576 base pair DNA probe prepared by using primers KDR-A: 5'-GGAATTCCATCCAAGCGGCAAATGTGTC-3' (SEQ ID NO:3) and KDR-B: 5'-GGAATTCCGAGTCTTCTAC-AAGGGTCTC-3' (SEQ ID NO:4). Lambda phage clones containing unique inserts were isolated through three rounds of replating and then characterized. The 3' 110 base pairs not represented in any of the isolated clones were cloned by PCR from the same library as above using the primers KDR-C: 5'-TTATGACAACACAGCAGG-3' (SEQ ID NO:5) and KDR-D: 5'-TTGGATCCTCGAGTTGGGGT-GTGGATGC'3' (SEQ ID NO:6). Overlapping clones were used to generate a full-length KDR gene into plasmid vector pGEM7Z. The gene contained an XhoI site at the 5' end which was changed to a BamHI site by first cutting with XhoI, then forming a blunt end with DNA polymerase and ligating an oligonucleotide BamHI linker and finally cloned as a BamHI/BamHI fragment back into pGEM7Z. The gene was sequenced on an ABI Prism automatic sequencer model number 377. In addition, the cytoplasmic domain of KDR which contains tyrosine kinase activity was cloned separately as a GST gene fusion into a baculovirus expression vector to characterize tyrosine kinase activity.

A variety of mammalian expression vectors may be used to express recombinant human KDR in mammalian cells. Expression vectors are defined herein as DNA sequences that are required for the transcription of cloned DNA and the translation of their mRNAs in an appropriate host. Such vectors can be used to express eukaryotic DNA in a variety of hosts such as bacteria, blue green algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

Commercially available mammalian expression vectors which may be suitable for recombinant human KDR expression, include but are not limited to, pcDNA3.1 (Invitrogen), pLITMUS28, pLITMUS29, pLITMUS38 and pLITMUS39 (New England Bioloabs), pcDNAI, pcDNAI-amp (Invitrogen), pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and λZD35 (ATCC 37565).

A variety of bacterial expression vectors may be used to express recombinant human KDR in bacterial cells. Commercially available bacterial expression vectors which may be suitable for recombinant human KDR expression include, but are not limited to pCR2.1 (Invitrogen), pET11a (Novagen), lambda gt11 (Invitrogen), and pKK223-3 (Pharmacia).

A variety of fungal cell expression vectors may be used to express recombinant human KDR in fungal cells. Commercially available fungal cell expression vectors which may be suitable for recombinant human KDR expression include but are not limited to pYES2 (Invitrogen) and *Pichia* expression vector (Invitrogen).

A variety of insect cell expression vectors may be used to express recombinant receptor in insect cells. Commercially available insect cell expression vectors which may be suitable for recombinant expression of human KDR include but are not limited to pBlueBacIII and pBlueBacHis2 (Invitrogen), and pAcG2T (Pharmingen).

An expression vector containing DNA encoding a human KDR-like protein may be used for expression of human KDR in a recombinant host cell. Recombinant host cells may be prokaryotic or eukaryotic, including but not limited to bacteria such as *E. coli,* fungal cells such as yeast, mammalian cells including but not limited to cell lines of human, bovine, porcine, monkey and rodent origin, and insect cells including but not limited to *Drosophila-* and silkworm-derived cell lines. Cell lines derived from mammalian species which may be suitable and which are commercially available, include but are not limited to, L cells L-M(TK⁻) (ATCC CCL 1.3), L cells L-M (ATCC CCL 1.2), Saos-2 (ATCC HTB-85), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171) and CPAE (ATCC CCL 209).

The expression vector may be introduced into host cells via any one of a number of techniques including but not limited to transformation, transfection, protoplast fusion, and electroporation. The expression vector-containing cells are individually analyzed to determine whether they produce human KDR protein. Identification of human KDR expressing cells may be done by several means, including but not limited to immunological reactivity with anti-human KDR antibodies, labeled ligand binding and the presence of host cell-associated human KDR activity.

The cloned human KDR cDNA obtained through the methods described above may be recombinantly expressed by molecular cloning into an expression vector (such as pcDNA3.1, pCR2.1, pBlueBacHis2 and pLITMUS28) containing a suitable promoter and other appropriate transcription regulatory elements, and transferred into prokaryotic or eukaryotic host cells to produce recombinant human KDR. Techniques for such manipulations can be found described in Sambrook, et al., supra, are discussed at length in the Example section and are well known and easily available to the artisan of ordinary skill in the art.

Expression of human KDR DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

To determine the human KDR cDNA sequence(s) that yields optimal levels of human KDR, cDNA molecules including but not limited to the following can be constructed: a cDNA fragment containing the full-length open reading frame for human KDR as well as various constructs containing portions of the cDNA encoding only specific domains of the protein or rearranged domains of the protein. All constructs can be designed to contain none, all or portions of the 5' and/or 3' untranslated region of a human KDR cDNA. The expression levels and activity of human KDR can be determined following the introduction, both singly and in combination, of these constructs into appropriate host cells. Following determination of the human KDR cDNA cassette yielding optimal expression in transient assays, this KDR cDNA construct is transferred to a variety of expression vectors (including recombinant viruses), including but not limited to those for mammalian cells, plant cells, insect cells, oocytes, bacteria, and yeast cells.

Levels of human KDR in host cells is quantified by a variety of techniques including, but not limited to, immunoaffinity and/or ligand affinity techniques. KDR-specific affinity beads or KDR-specific antibodies are used to isolate $^{35}$S-methionine labeled or unlabelled KDR. Labeled KDR protein is analyzed by SDS-PAGE. Unlabelled KDR protein is detected by Western blotting, ELISA or RIA assays employing either KDR protein specific antibodies and/or antiphosphotyrosine antibodies.

Following expression of KDR in a host cell, KDR protein may be recovered to provide KDR protein in active form. Several KDR protein purification procedures are available and suitable for use. Recombinant KDR protein may be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography.

In addition, recombinant KDR protein can be separated from other cellular proteins by use of an immunoaffinity column made with monoclonal or polyclonal antibodies specific for full-length KDR protein, or polypeptide fragments of KDR protein. Additionally, polyclonal or monoclonal antibodies may be raised against a synthetic peptide (usually from about 9 to about 25 amino acids in length) from a portion of the protein as disclosed in SEQ ID NO:2. Monospecific antibodies to human KDR are purified from mammalian antisera containing antibodies reactive against human KDR or are prepared as monoclonal antibodies reactive with human KDR using the technique of Kohler and Milstein (1975, *Nature* 256: 495–497). Monospecific antibody as used herein is defined as a single antibody species or multiple antibody species with homogenous binding characteristics for human KDR. Homogenous binding as used herein refers to the ability of the antibody species to bind to a specific antigen or epitope, such as those associated with human KDR, as described above. Human KDR-specific antibodies are raised by immunizing animals such as mice, rats, guinea pigs, rabbits, goats, horses and the like, with an appropriate concentration of human KDR protein or a synthetic peptide generated from a portion of human KDR with or without an immune adjuvant.

Preimmune serum is collected prior to the first immunization. Each animal receives between about 0.1 μg and about 1000 μg of human KDR protein associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of human KDR protein or peptide fragment thereof in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of human KDR in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with human KDR are prepared by immunizing inbred mice, preferably Balb/c, with human KDR protein. The mice are immunized by the IP or SC route with about 1 μg to about 100 μg, preferably about 10 μg, of human KDR protein in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 1 to about 100 μg of human KDR in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected form growth positive wells on about days 14, 18, and 21 and are screened for antibody production by an immunoassay such as solid phase immunoradioassay (SPIRA) using human KDR as the antigen. The culture fluids are also tested in the Ouchterlony precipitation assay to determine the isotype of the mAb. Hybridoma cells from antibody positive wells are cloned by a technique such as the soft agar technique of MacPherson, 1973, Soft Agar Techniques, in *Tissue Culture Methods and Applications*, Kruse and Paterson, Eds., Academic Press.

Monoclonal antibodies are produced in vivo by injection of pristine primed Balb/c mice, approximately 0.5 ml per mouse, with about 2×10$^6$ to about 6×10$^6$ hybridoma cells about 4 days after priming. Ascites fluid is collected at approximately 8–12 days after cell transfer and the monoclonal antibodies are purified by techniques known in the art.

In vitro production of anti-human KDR mAb is carried out by growing the hydridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of human KDR in body fluids or tissue and cell extracts.

It is readily apparent to those skilled in the art that the above described methods for producing monospecific antibodies may be utilized to produce antibodies specific for human KDR peptide fragments, or full-length human KDR.

Human KDR antibody affinity columns are made, for example, by adding the antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) and the cell culture supernatants or cell extracts containing full-length human KDR or human KDR protein fragments are slowly passed through the column. The column is then washed with phosphate buffered saline until the optical density ($A_{280}$) falls to background, then the protein is eluted with 0.23 M glycine-HCl (pH 2.6). The purified human KDR protein is then dialyzed against phosphate buffered saline.

The human KDR protein of the present invention is suitable for use in an assay procedure for the identification of compounds which modulate KDR activity. A KDR-containing fusion construct, such as a GST-KDR fusion as discussed within this specification, is useful to measure KDR activity. Kinase activity is, for example, measured by incorporation of radiolabeled phosphate into polyglutamic acid, tyrosine, 4:1 (pEY) substrate. The phosphorylated pEY product is trapped onto a filter membrane and the incorporation of radiolabeled phosphate quantified by scintillation counting. Soluble recombinant GST-kinase domain fusion proteins are expressed in Sf21 insect cells (Invitrogen) using a baculovirus expression vector (pAcG2T, Pharmingen). A lysis buffer is 50 mM Tris, pH 7.4, 0.5 M NaCl, 5 mM DTT, 1 mM EDTA, 0.5% Triton X-100, 10% glycerol, 10 µg/ml of each leupeptin, pepstatin and aprotinin and 1 mM phenylmethylsulfonyl fluoride (all Sigma). A wash buffer is 50 mM Tris, pH 7.4, 0.5 M NaCl, 5 mM DTT, 1 mM EDTA, 0.05% Triton X-100, 10% glycerol, 10 µg/ml of each leupeptin, pepstatin and aprotinin and 1 mM phenylmethylsulfonyl fluoride. A dialysis buffer is 50 mM Tris, pH 7.4, 0.5 M NaCl, 5 mM DTT, 1 mM EDTA, 0.05% Triton X-100, 50% glycerol, 10 µg/ml of each leupeptin, pepstatin and aprotinin and 1 mM phenylmethylsuflonyl fluoride. A 10× reaction buffer is 200 mM Tris, pH 7.4, 1.0 M NaCl, 50 mM $MnCl_2$, 10 mM DTT and 5 mg/ml bovine serum albumin (Sigma). An enzyme dilution buffer is 50 mM Tris, pH 7.4, 0.1 M NaCl, 1 mM DTT, 10% glycerol, 100 mg/ml BSA. A 10× substrate solution would be 750 µg/ml poly(glutamic acid, tyrosine; 4:1) (Sigma); stop solution is 30% trichloroacetic acid, 0.2 M sodium pyrophosphate (both Fisher) and wash solution is 15% trichloroacetic acid, 0.2 M sodium pyrophosphate. The filter plates are Millipore #MAFC NOB, GF/C glass fiber 96 well plates.

First, Sf21 cells are infected with recombinant virus at a multiplicity of infection of 5 virus particles/cell and grown at 27° C. for 48 hours. All subsequent steps are performed at 4° C. Infected cells are harvested by centrifugation at 1000×g and lysed at 4° C. for 30 minutes with 1/10 volume of lysis buffer followed by centrifugation at 100,000×g for 1 hour. The supernatant is then passed over a glutathione-Sepharose column (Pharmacia) equilibrated in lysis buffer and washed with 5 volumes of the same buffer followed by 5 volumes of wash buffer. Recombinant GST-KDR protein is eluted with wash buffer/10 mM reduced glutathione (Sigma) and dialyzed against dialysis buffer.

The KDR assay comprises the following steps:

1. Add 5 µl of inhibitor or control to the assay in 50% DMSO;

2. Add 35 µl of reaction mix containing 5 µl of 10× reaction buffer, 5 µl 25 mM ATP/10 µCi [$^{33}$P]ATP (Amersham), and 5 µl 10× substrate;

3. Start the reaction by the addition of 10 µl of KDR (25 nM) in enzyme dilution buffer;

4. Mix and incubate at room temperature (~22° C.) for 15 minutes;

5. Stop by the addition of 50 µl stop solution;

6. Incubate for 15 minutes at 4° C.;

7. Transfer a 90 µl aliquot to filter plate;

8. Aspirate and wash 3 times with 100 µl of wash solution;

9. Add 30 µl of scintillation cocktail, seal plate and count in a Wallac Microbeta scintillation counter.

Modulating KDR includes the inhibition or activation of the kinase which affects the mitogenic function of VEGF. Compounds which modulate KDR include agonists and antagonists.

Therefore, the human KDR protein of the present invention may be obtained from both native and recombinant sources (as a full-length protein, biologically active protein fragment, or fusion construction) for use in an assay procedure to identify human KDR modulators. In general, an assay procedure to identify human KDR modulators will contain the intracelluar domain of human KDR, and a test compound or sample which contains a putative KDR kinase agonist or antagonist. The test compounds or samples may be tested directly on, for example, purified KDR, KDR kinase or a GST-KDR kinase fusion, subcellular fractions of KDR-producing cells whether native or recombinant, whole cells expressing human KDR whether native or recombinant, intracellular KDR protein fragments and respective deletion fragments, and/or extracellular intracellular KDR protein fragments and respective deletion fragments. The test compound or sample may be added to KDR in the presence or absence of a known human KDR substrate. The modulating activity of the test compound or sample may be determined by, for example, analyzing the ability of the test compound or sample to bind to the KDR intracellular domain, activate the protein, inhibit the protein, inhibit or enhance the binding of other compounds to human KDR, modifying VEGF receptor regulation, or modifying kinase activity.

Therefore, the present invention also relates to subcellular membrane fractions of the recombinant host cells (both prokaryotic and eukaryotic as well as both stably and transiently transformed cells) comprising the nucleic acids of the present invention. These subcellular membrane fractions will comprise human KDR at levels substantially above wild-type levels and hence will be useful in various assays described throughout this specification.

The identification of modulators of human KDR will be useful in treating various disease states. For example, vascular growth in or near the retina leads to visual degeneration culminating in blindness. VEGF accounts for most of the angiogenic activity produced in or near the retina in diabetic retinopathy. Ocular VEGF mRNA and protein are elevated by conditions such as retinal vein occlusion in primates and decreased $pO_2$ levels in mice that lead to neovascularization. Expression of VEGF is also significantly increased in hypoxic regions of animal and human tumors adjacent to areas of necrosis. VEGF contributes to tumor growth in vivo by promoting angiogenesis through its paracrine vascular endothelial cell chemotactic and mitogenic activities. Inhibition of KDR is implicated in pathological neoangiogenesis, and compounds which inhibit the mitogenic activity of VEGF via inhibition of KDR will be useful in the treatment of diseases in which neoangiogenesis is part of the overall pathology, such as diabetic retinal vascularization, various forms of cancer and inflammation which demonstrate high levels of gene and protein expression. Examples of such cancers include cancers of the brain, breast, genitourinary tract, lymphatic system, stomach, intestines including colon, pancreas, prostate, larynx and lung. These include histiocytic lymphoma, lung adenocarcinoma, glioblastoma and small cell lung cancers. Examples of inflammation include rheumatoid arthritis, psoriasis, contact dermatis and hypersensitivity reactions.

The present invention also relates to gene transfer of a DNA vector and concomitant in vivo expression of an extracelluar, soluble form of human KDR, preferably comprising from about amino acid 1 to from about amino acid 644 (to encompass the initial six IG-like extracellular domains) to about amino acid 763 (to encompass all seven IG-like extracellular domains) of human KDR as set forth in SEQ ID NO:2. Such a gene therapy vehicle will express this soluble form of human KDR, which binds VEGF or a VEGF homologue in and around the localized site of the disorder. The formation of a sKDR/VEGF complex will inhibit binding of VEGF to the KDR and FLT-1 tyrosine kinase receptors spanning the vascular endothelial cell membrane, thus preventing initiation of the signal transduction stimulating angiogenesis. In addition, expression of sKDR may also impart a therapeutic effect by binding to membrane associated VEGF receptors. VEGF receptors are thought to be dimerized by binding dimeric VEGF ligand which in turn allows the receptor intracellular tyrosine kinase domains to transphosphorylate each other generating phosphorylated tyrosine residues that facilitate the subsequent binding and activation of downstream signal transduction proteins. Soluble KDR will be able to form heterodimers with full-length VEGF receptors that, because the sKDR forms are devoid of an intracellular tyrosine kinase region, prevent receptor tyrosine kinase domain transphosphorylation, the initiation of signal transduction and thus VEGF-induced mitogenesis and angiogenesis in a dominant negative manner. The skilled artisan will be able to generate various gene therapy constructs which express various regions of the extracellular domain of KDR for administration to the patient. While the patient may be any mammalian host, the preferable treatment is directed toward humans. Any such construct will express a KDR fragment which effectively inhibits mitogenic activity associated with VEGF/KDR associations on human endothelial cells. It is preferred in the present invention that this region comprise an isolated nucleic acid molecule which encodes from about amino acid 1 to about amino acid 644 and/or from about amino acid 1 to about amino acid 763 as set forth in SEQ ID NO:2.

Another preferred embodiment of the present invention is a nucleic acid molecule which encodes an extracellular-transmembrane KDR protein fragment which is also useful in gene therapy applications as described in the previous paragraph. It is preferred that any such DNA molecule comprise a DNA sequence from which encodes from about amino acid 1 to about amino acid about the initial 785–795 amino acids of KDR as set forth in SEQ ID NO:2, and especially preferred is an isolated nucleic acid molecule construction which encodes the amino terminal portion of KDR with a truncation at about amino acid 791 as set forth in SEQ ID NO:2.

One preferred gene therapy application for the human KDR gene and protein of the present invention relates to promoting inhibition of solid tumor angiogenesis and metastasis by utilizing the disclosed gene therapy methodology. A second preferred gene therapy application for the human KDR gene and protein of the present invention relates to promoting inhibition of diabetic retinopothy, as described elsewhere within this specification. The transferred sKDR nucleic acid is expressed within the region of interest subsequent to gene transfer such that expressed sKDR binds to VEGF to prevent binding of VEGF to the KDR and FLT-1 tyrosine kinase receptors, antagonizing transduction of the normal intracellular signals associated with vascular endothelial cell-induced tumor angiogenesis and diabetic retinopathy.

The present invention is also directed to methods for screening for compounds which modulate the expression of DNA or RNA encoding a human KDR protein. Compounds which modulate these activities may be DNA, RNA, peptides, proteins, or non-proteinaceous organic molecules. Compounds may modulate by increasing or attenuating the expression of DNA or RNA encoding human KDR, or the function of human KDR. Compounds that modulate the expression of DNA or RNA encoding human KDR or the biological function thereof may be detected by a variety of assays. The assay may be a simple "yes/no" assay to determine whether there is a change in expression or function. The assay may be made quantitative by comparing the expression or function of a test sample with the levels of expression or function in a standard sample. Kits containing human KDR, antibodies to human KDR, or modified human KDR may be prepared by known methods for such uses.

The DNA molecules, RNA molecules, recombinant protein and antibodies of the present invention may be used to screen and measure levels of human KDR. The recombinant proteins, DNA molecules, RNA molecules and antibodies lend themselves to the formulation of kits suitable for the detection and typing of human KDR. Such a kit would comprise a compartmentalized carrier suitable to hold in close confinement at least one container. The carrier would further comprise reagents such as recombinant KDR or anti-KDR antibodies suitable for detecting human KDR. The carrier may also contain a means for detection such as labeled antigen or enzyme substrates or the like.

Pharmaceutically useful compositions comprising modulators of human KDR may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, modified human KDR, or either KDR agonsits or antagonists including tyrosine kinase activators or inhibitors.

Therapeutic or diagnostic compositions of the invention are administered to an individual in amounts sufficient to treat or diagnose disorders. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages. Alternatively, co-administration or sequential administration of other agents may be desirable.

The present invention also has the objective of providing suitable topical, oral, systemic and parenteral pharmaceutical formulations for use in the novel methods of treatment of the present invention. The compositions containing compounds identified according to this invention as the active ingredient can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal, hepatic and cardiovascular function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

The following examples are provided to illustrate the present invention without, however, limiting the same hereto.

EXAMPLE 1

Isolation of a cDNA Encoding Human KDR

Materials

A human umbilical vein endothelial cell lambda phage cDNA library was purchased from Clonetech (Cat. #HL1070b). DNA modification and restriction enzymes were purchased from Promega. Plasmid pGEM7Z was purchased from Promega (Cat. #P2251). Taq polymerase was from Perkin Elmer Cetus (part number N801-0055). BamHI linkers were purchased from New England Biolabs (Cat. #1071). [$\alpha$-$^{32}$P] dATP was purchased from Amersham (Cat. # PB 10204). Rediprime was also purchased from Amersham (Cat. # RPN 1633). The baculovirus expression vector pAcG2T was purchased from Pharmingen (Cat. # 21414P).

The PCR primers used are as follows:

KDR-A 5'-GGAATTCCATCCAAGCGGCAAATGTGTC-3' (SEQ ID NO:3);
KDR-B 5'-GGAATTCCGAGTCTTCTACAAGGGTCTC-3' (SEQ ID NO:4)
KDR-C 5'-TTATGACAACACAGCAGG-3' (SEQ ID NO:5); and,
KDR-D 5'-TTGGATCCTCGAGTTGGGGTGTGGATGC-3' (SEQ ID NO:6).

Methods: Gene Cloning

The KDR cDNA was isolated by probing a human umbilical vein endothelial cell lambda phage cDNA library from Clonetech with a KDR-specific 576 base pair DNA probe. The probe was prepared by PCR using primers KDR-A/KDR-B and Taq polymerase, then labeled to a specific activity of $1 \times 10^7$ cpm/ng by random priming. Phage were plated at about 50,000 plaques/plate and hybridization was done by standard protocols. A total of $1 \times 10^6$ phage were screened. Lambda phage clones containing unique inserts were isolated through three rounds of replating and then characterized. The 3' 110 base pairs not represented in any of the isolated clones were cloned by PCR from the same library as above using the primers KDR-C and KDR-D. Overlapping clones were used to generate a full-length KDR gene by restriction enzyme digestion, isolation of the individual gene fragments and ligation (restriction enzymes and ligase were from Promega) into pGEM7Z. The gene contained an XhoI site at the 5' end which was changed to a BamHI site by first cutting with XhoI, then forming a blunt end with DNA polymerase and ligating an oligonucleotide BamHI linker and finally cloned as a BamHI/BamHI fragment back into pGEM7Z. The gene was sequenced on an ABI Prism automatic sequencer model number 377. The cDNA sequence of human KDR is shown in FIGS. 1A and 1B. The deduced amino acid sequence of human KDR is shown in FIG. 2.

EXAMPLE 2

Construction of GST/KDR-1

The cytoplasmic domain of KDR which contains tyrosine kinase activity was cloned separately as a glutathione S-transferase (GST) gene fusion into a baculovirus expression vector to characterize tyrosine kinase activity. To construct this GST fusion, a Kpn I cloning site was introduced into the KDR gene by changing the codons encoding residues Gly 800 (GGG to GGC) and Leu 802 (TTG to CTG) and the existing BamHI site was removed by changing the codon encoding Asp 807 (GAT to GAC); these changes are silent and do not change the amino acid sequence of the receptor. A new BamHI site was introduced to form an in frame fusion with the carboxyl terminus of GST and KDR at Ala 792. The GST and KDR BamHI-digested fragments were ligated to generated the in frame GST/KDR fusion. Active GST-KDR tyrosine kinase protein is produced in insect cells.

EXAMPLE 3

Construction of KDR Core Kinase Domain

The kinase domain of KDR was cloned using the preexisting BamHI site at the 5' end of the kinase domain and introducing a stop codon followed by a SalI site at the 3' end of the kinase domain (Tyr 1175 TAC changed to TAA). KDR DNA was used as a template in a PCR reaction with primers KDR-E (5'-GGATCCAGATGAACTCCCATTG-3' [SEQ ID NO:7]) and KDR-F (5'-GTCGACTTAGTCTTTGCCAT-CCTGCTGAGC-3' [SEQ ID NO:8]). The resulting KDR core kinase BamHI/Sal I fragment was cloned into pBlueBacHis2B, this creates an inframe fusion of the methionine initiator codon and the poly histidine sequence of the vector with the KDR kinase domain. This vector, pBBH-KDR-1, also provides an enterokinase recognition site to remove the His tag polypeptide by proteolysis. The KDR core kinase protein was expressed in insect cells and purified on a nickel chelating column. The purified KDR core kinase was active in the kinase assay described herein.

EXAMPLE 4

Molecular Modeling of Human KDR

The cytoplasmic domain of the VEGF receptor was aligned by hand to the sequence of FGFR1 as taken from the published crystal structure (Mohammadi, M., Schlessinger, J. and Hubbard, S. R., 1996, Cell 86: 577). The sequences are ~60% identical in this alignment. An homology model of KDR kinase was then built in Quanta (version 4.1p) by copying the coordinates from the FGFR1/AMP-PCP crystal structure. The kinase insert region (residues 933–1006 in KDR) was not included in the model since there was no unique conformation for this region in the crystal structure. The homology model was then minimized using CHARMM within Quanta constraining the protein backbone and allowing the side chains to move freely.

Figure 3B:
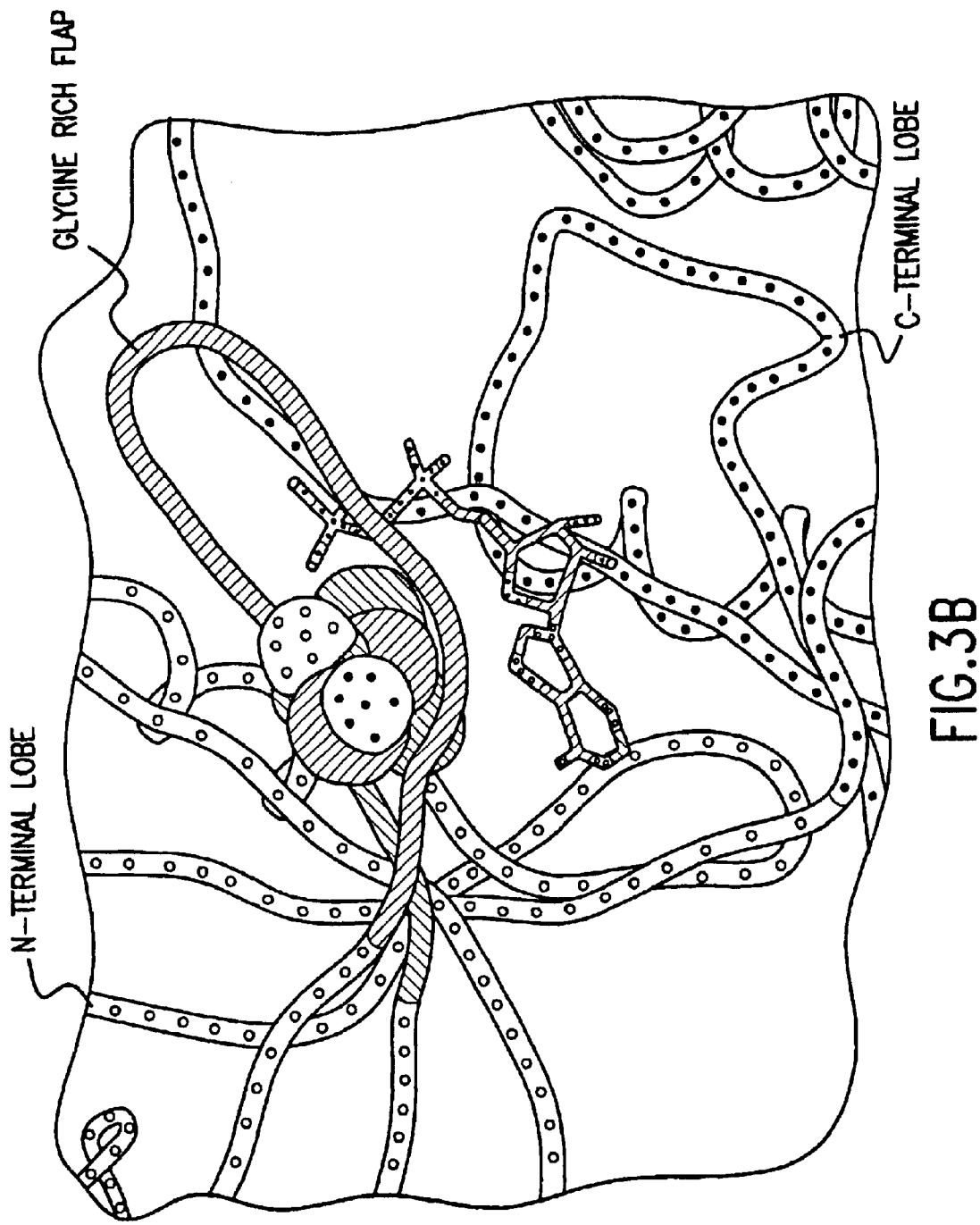
FIG. 3B shows ATP binding domain from the KDR homology model with bound AMP-PCP. The side chain of V848 forms hydrophobic contacts with the adenine from AMP-PCP. The gamma phosphate of AMP-PCP is not visible. The protein carbon alpha trace is shown in pipes, the AMP-PCP in sticks and the V848 side chain in space filling. The N-terminal lobe is colored blue (or alternatively labeled with light circles) with the exception of the glycine rich flap which is colored green (or alternatively labeled as a lined region). The C-terminal lobe is colored red (or alternatively labeled with dark circles).

The change of amino acid residue 848 from the published Glu to Val in SEQ ID NO:2 is found in the glycine-rich flap, which forms part of the ATP binding pocket. The highly conserved Val is found to form hydrophobic contacts to ATP in other kinases, and appears to be positioned to form these same contacts in KDR. A charged Glu in this position is not likely to make proper contact with ATP. This is shown by computer modeling in FIG. 3A and FIG. 3B. FIG. 3A shows the ATP binding domain from the KDR V848E mutant homology model with bound AMP-PCP. The side chain of E848 is in contact the adenine from AMP-PCP. The gamma phosphate of AMP-PCP is not visible. The protein carbon alpha trace is shown in pipes, the AMP-PCP in sticks and the E848 side chain in space filling. The N-terminal lobe is colored blue (or alternatively labeled with light circles) with the exception of the glycine rich flap which is colored green (or alternatively labeled as a lined region). The C-terminal lobe is colored red (or alternatively labeled with dark circles). FIG. 3B shows ATP binding domain from the KDR homology model with bound AMP-PCP. The side chain of V848 forms hydrophobic contacts with the adenine from AMP-PCP. The gamma phosphate of AMP-PCP is not visible. The protein carbon alpha trace is shown in pipes, the AMP-PCP in sticks and the V848 side chain in space filling. The N-terminal lobe is colored blue (or alternatively labeled with light circles) with the exception of the glycine rich flap which is colored green (or alternatively labeled as a lined region). The C-terminal lobe is colored red (or alternatively labeled with dark circles).

EXAMPLE 5

Tyrosine Phosphorylation of KDRcyt Mutants

Figure 4A:
FIGS. 4A and 4B show that purified GST-$KDR_{cyt}$E848 was unable to autophosphorylate in the presence of 1-mM ATP wherein 12 ng of GST-$KDR_{cyt}$V848 in the presence of 1 mM ATP resulted in autophosphorylation (FIG. 4A) and that both 120 ng of GST-$KDR_{cyt}$E848 and 12 ng of GST-$KDR_{cyt}$V848 react with anti-KDR antibody (FIG. 4B).
Figure 4B:

Purified $KDR_{cyt}E848$ and $KDR_{cyt}V848$ were incubated with at concentrations of 12 ng or 120 ng, respectively, or without 1 mM ATP at 37° C. for 10 min. The reaction was stopped by the addition of an equal volume of 2× SDS-PAGE sample buffer and boiled for 5 min. Reaction products were separated by 7.5%/SDS-PAGE and analyzed by Western blot probed with the antiphosphotyrosine antibody PY20 (Transduction Laboratories; FIG. 4A), or an anti-KDR antibody (Santa Cruz Biotechnology; FIG. 4B) visualized using the ECL detection kit and quantified by scanning with a densitometer (Molecular Dynamics). FIG. 4A shows that purified $GST-KDR_{cyt}E848$ was unable to autophosphorylate in the presence of 1-mM ATP wherein 12 ng of $GST-KDR_{cyt}V848$ in the presence of 1 mM ATP resulted in autophosphorylation. FIG. 4B shows a signal against anti-KDR antibody for 120 ng $GST-KDR_{cyt}E848$ and 12 ng of $GST-KDR_{cyt}V848$.

What is claimed:

1. A membrane preparation comprising the human KDR protein which consists of the amino acid sequence as set forth in SEQ ID NO: 2, wherein said membrane preparation is obtained from a recombinant host cell transformed or transfected with a DNA molecule encoding the human KDR protein.

2. A membrane preparation comprising a KDR protein fragment which comprises an intracellular portion of a human KDR protein from about amino acid 790 to about amino acid 1356 as set forth in SEQ ID NO: 2, wherein position 848 is a valine residue, wherein said membrane preparation is obtained from a recombinant host cell transformed or transfected with a DNA molecule encoding the human KDR protein fragment.

3. The membrane preparation of claim 2, wherein position 772 is an alanine residue, position 787 is an arginine residue, position 835 is a lysine residue, position 848 is a valine residue and position 1347 is a serine residue, wherein said membrane preparation is obtained from a recombinant host cell transformed or transfected with a DNA molecule encoding the human KDR protein fragment.

4. A membrane preparation comprising a KDR fusion protein comprising a KDR protein and a heterologous protein, wherein the KDR protein comprises an intracellular portion of a human KDR protein from about amino acid 790 to about amino acid 1356 as set forth in SEQ ID NO: 2, wherein position 848 is a valine, wherein said membrane preparation is obtained from a recombinant host cell transformed or transfected with a DNA molecule encoding the human KDR fusion protein. said membrane preparation is obtained from a recombinant host cell transformed or transfected with a DNA molecule encoding the human KDR fusion protein.

5. The membrane preparation of claim 4, wherein position 772 is an alanine residue, position 787 is an arginine residue, position 835 is a lysine residue, position 848 is a valine residue and position 1347 is a serine residue, wherein said membrane preparation is obtained from a recombinant host cell transformed or transfected with a DNA molecule encoding the human KDR fusion protein.

6. A membrane preparation according to claim 5 wherein the heterologous protein is GST.

* * * * *